US007521595B2

(12) United States Patent
Hannoufa et al.

(10) Patent No.: US 7,521,595 B2
(45) Date of Patent: Apr. 21, 2009

(54) REPRESSOR-MEDIATED REGULATION SYSTEM FOR CONTROL OF GENE EXPRESSION IN PLANTS

(75) Inventors: Abdelali Hannoufa, Saskatoon (CA); Dwayne Hegedus, Saskatoon (CA); Nicholas Bate, Urbandale, IA (US)

(73) Assignee: Her Majesty the Queen in right of Canada, as represented by the Minister of Agriculture and Agri-Food, Ottawa, Ontario (CA)

( * ) Notice: Subject to any disclaimer, the term of this patent is extended or adjusted under 35 U.S.C. 154(b) by 0 days.

(21) Appl. No.: 10/995,951

(22) Filed: Nov. 23, 2004

(65) Prior Publication Data

US 2005/0245732 A1 Nov. 3, 2005

Related U.S. Application Data

(63) Continuation of application No. PCT/CA02/01807, filed on Nov. 21, 2002.

(30) Foreign Application Priority Data

May 23, 2002 (WO) ...................... PCT/CA02/00740

(51) Int. Cl.
 C12N 15/82 (2006.01)
 C12N 15/63 (2006.01)
 C12N 15/31 (2006.01)
 C12N 15/00 (2006.01)
 A01H 5/10 (2006.01)
(52) U.S. Cl. ........................ 800/288; 800/298; 435/468; 435/320.1; 536/23.1; 536/23.2; 536/23.7; 536/24.1
(58) Field of Classification Search ........................ None
 See application file for complete search history.

(56) References Cited

U.S. PATENT DOCUMENTS 5,428,147 A 6/1995 Barker et al. ................ 536/24.1

FOREIGN PATENT DOCUMENTS

WO WO 98/37184 8/1998

OTHER PUBLICATIONS

Archdeacon et al 2000 FEMS Microbiology Letters 187:175-178.*
Cooley et al 1991 J. Bacteriol. 173:2608-2616.*
Ulmasov et al 1997 The Plant Cell 9:1963-1971.*
Chou et al., "Agrobacterium transcriptional regulator Ros is a prokaryotic zinc finger protein that regulates the plant oncogene *ipt*," Proc. Natl. Acad. Sci. USA, 95:5293-5298 (1998).
Bouhouche et al., "The origin of prokaryotic C2H2 zinc finger regulators," Trends in Microbiology, vol. 8, No. 2, pp. 77-81, (2000).
Zuo et al., "Chemical-inducible systems for regulated expression of plant genes," Current Opinion in Biotechnology vol 11 pp. 146-151 (2000).
An et al., "Strong, constitutive expression of the *Arabidopsis* ACT/ACT8 actin subclass in vegetative tissues," The Plant Journal, 10(1), 107-121 (1996).
Aoyama et al., "A glucocorticoid-mediated transcriptional induction system in trasngenic plants," The Plant Journal, 11(3), 605-612 (1997).
Archdeacon et al., "A single amino acid substitution beyond the C2H2-zinc finger in Ros derepresses virulence and T-DNA genes in *Agrobacterium tumefaciens*," FEMS Microbiology Letters, 187, 175-178 (2000).
Beetham et al., "A tool for functional plant geomics: Chimeric RNA/DNA oligonucleotides cause in vivo gene-specific mutations," Proc. Natl. Acad. Sci. USA, 96, 8774-8778 (1999).
Bittinger et al., "rosR, a Determinant of Nodulation Competitiveness in *Rhizobium etli*," Molecular Plant-Microbe Interactions, 10(2), 180-186 (1997).
Brandstatter et al., "Two Genes with Similarity to Bacterial Response Regulators Are Rapidly and Specifically Induced by Cytokinin in Arabidopsis," The Plant Cell, 10, 1009-1019 (1998).
Brightwell et al., "Pleiotropic Effects of Regulatory ros Mutants of *Agrobacterium radiobacter* and Their Interaction with Fe and Glucose," Molecular Plant-Microbe Interactions, 8(5), 747-754 (1995).
Caddick et al., "An ethanol inducible gene switch for plants used to manipulate carbon metabolism," Nature Biotechnology, 16, 177-180 (1998).
Carrington et al., "Bipartite Signal Sequence Mediates Nuclear Translocation of the Plant Potyviral Nla Protein," The Plant Cell, 3, 953-962 (1991).
Clough et al.,., "Floral dip: a simplified method for *Agrobacterium*-mediated transformation of *Arabidopis thaliana*," The Plant Journal, 16(6),735-743 (1998).
Cooley et al., "The *virC* and *virD* Operons of the *Agrobacterium* Ti Plasmid Are Regulated by the ros Chromosomal Gene: Analysis of the Cloned *ros* Gene," Journal of Bacteriology, 173(8), pp. 2608-2616 (1991).
Cornejo et al., "Activity of a maize ubiquitin promoter in transgenic rice," Plant Molecular Biology, 23, 567-581 (1993).

(Continued)

*Primary Examiner*—Phuong Bui
*Assistant Examiner*—Brent Page
(74) *Attorney, Agent, or Firm*—Heslin Rothenberg Farley & Mesiti P.C.

(57) ABSTRACT

The invention provides a method for selectively controlling the transcription of a gene of interest, comprising producing one or more plants that express either a first, a second, or both the first and second genetic constructs. The first genetic construct comprises a first regulatory region operatively linked to a gene of interest and at least one repressor sequence capable of controlling the activity of the first regulatory region. The second genetic construct comprises a second regulatory region in operative association with a nucleic acid molecule, or a derivative thereof, encoding a repressor protein, the repressor protein exhibiting both repressor operator sequence binding activity and repressor activity.

20 Claims, 25 Drawing Sheets

OTHER PUBLICATIONS

D'Souza-Ault et al., "Analysis of the Ros Repressor of *Agrobacterium virC* and *virD* Operons: Molecular Intercommunication between Plasmid and Chromosomal Genes," Journal of Bacteriology, 175(11),3486-3490 (1993).

Eisner et al., "Analysis of Arabidopsis thaliana transgenic plants transformed with *CER2* and *CER3* genes in sense and antisense orientations," Theor Appl Genet, 97, 801-809 (1998).

Gatz et al., "Promoters that respond to chemical inducers," Trends in Plant Science, 3(9), 352-358 (1998).

Gatz, "Chemical Control of Gene Expression," Annu. Rev. Plant Physiol. Mol. Biol. , 48, 89-108 (1997).

Grierson et al., "Plant Molecular Biology," Tertiary Level Biology, Second Edition, published by Blackie, Glasgow and London, published in the USA by Chapman and Hall New York, Chapter 7, pp. 141-211.

Holtorf et al., "Comparison of different constitutive and inducible promoters for the overexpression of transgenes in *Arabidopsis thaliana*," Plant Molecular Biology, 29, 637-646 (1995).

Jofuku et al., "Control of Arabidopsis Flower and Seed Development by the Homeotic Gene *APETALA2*," The Plant Cell, 6, 1211-1225 (1994).

Kakimoto, "CKI1, a Histidine Kinase Homolog Implicated in Cytokinin Signal Transduction," Science, 274, 982-985 (1996).

Keller et al., "Molecular Analysis of the *Rhizobium meliloti mucR* Gene Regulating the Biosynthesis of the Exopolysaccharides Succinoglycan and Galactoglucan," Molecular Plant-Microbe Interactions, 8(2), 267-277 (1995).

Kohno-Murase et al., "Effects of an antisense napin gene on seed storage compounds in trasngenic *Brassica napus* seeds," Plant Molecular Biology, 26, 1115-1124 (1994).

Lotan et al., "Arabidopsis Leafy Cotyledon1 Is Sufficient to Induce Embryo Development in Vegetative Cells," Cell, 93, 1195-1205 (1998).

Lusser et al., "Histone acetylation: lessons from the plant kingdom," Trends in Plant Science, 6(2), 59-65 (2001).

Mandel et al., "Definition of constitutive gene expression in plants: the translation initation factor 4A gene as a model," Plant Molecular Biology, 29, 995-1004 (1995).

Miki et al., "Fundamentals of gene transfer in plants," in Plant Metabolism edited by Dennis et al., Longman Press, 561-579.

Murray et al., "Codon usage in plant genes," Nucleic Acids Research, 17(2), 477-497 (1989).

Odell et al., "Identification of DNA sequences required for activity of the cauliflower mosaic virus 35S promoter," Nature, 313, 810-812 (1985).

Ogas et al., "Cellular Differentiation Regulated by Gibberellin in the *Arabidopsis thaliana pickle* Mutant," Science, 277, 91-94 (1997).

Rizzo et al., "Unique Strains of SV40 in Commercial Poliovaccines from 1955 Not Readily Identifiable with Current Testing for SV40 Infection," Cancer Research, 59, 6103-6108 (1999).

Robbins et al., "Two Interdependent Basic Domains in Nucleoplasmin Nuclear Targeting Sequence: Identification of a Class of Bipartite Nuclear Targeting Sequence," Cell, 64, 615-623 (1991).

Salter et al., "Characterisation of the ethanol-inducible *alc* gene expression system for transgenic plants," The Plant Journal, 16(1), 127-132 (1998).

Sardana et al., "Construction and rapid testing of synthetic and modified toxin gene sequences *CryIA* (*b* & *c*) by expression in maize endosperm culture," Plant Cell Reports, 15, 677-681 (1996).

Ulmasov et al., "Aux/IAA Proteins Repress Expression of Reporter Genes Containing Natural and Highly Active Synthetic Auxin Response Elements," The Plant Cell, 9, 1963-1971 (1997).

van der Krol et al., "The Basic Domain of Plant B-ZIP Proteins Facilitates Import of a Reporter Protein into Plant Nuclei," The Plant Cell, 3, 667-675 (1991).

Varagona et al., "Nuclear Localization Signal(s) Required for Nuclear Targeting of the Maize Regulatory Protein Opaque-2," The Plant Cell, 4, 1213-1227 (1992).

Rogers et al., "Gene Transfer in Plants: Production of Transformed Plants Using Ti Plasmid Vectors," in Methods For Plant Molecular Biology, Section VIII, [26] 423-463, edited by Weissbach & Weissbach, Academic Press, Inc. (1988).

Xu et al., "Rice Triosephosphate Isomerase Gene 5' Sequence Directs β-Glucuronidase Activity in Transgenic Tobacco but Requires an Intron for Expression in Rice," Plant Physiol. 106, 459-467 (1994).

Yanofsky et al., "The protein encoded by the *Arabidopsis* homeotic gene agamous resembles transcription factors," Nature, 346, 35-39 (1990).

Zhang et al., "Analysis of Rice *Act1* 5' Region Activity in Transgenic Rice Plants," The Plant Cell, 3, 1155-1165 (1991).

Zhu et al., "Targeted manipulation of maize genes in vivo using chimeric RNA/DNA oligonucleotides," Proc. Natl. Acad. Sci. USA, 96, 8768-8773 (1999).

Hannoufa et al., pending U.S. Appl. No. 10/719,996, filed Nov. 21, 2003, entitled "A Repressor-Mediated Regulation System For Control of Gene Expression in Plants".

* cited by examiner

| | | | | | | | | | | | | | | |
|---|---|---|---|---|---|---|---|---|---|---|---|---|---|---|
| M | T | E | T | A | Y | G | N | A | Q | D | L | L | V | E | WT-ROS |
| M | T | E | T | A | Y | G | N | A | Q | D | L | L | V | E | SYNROS |
| M | T | D | M | A | T | G | N | A | P | E | L | L | V | E | ROS-R |
| M | T | E | T | A | Y | G | N | A | Q | D | L | L | V | E | ROS-AR |
| M | T | <u>E</u> | <u>T</u> | <u>S</u> | <u>L</u> | G | <u>T</u> | <u>S</u> | <u>N</u> | <u>E</u> | L | L | V | E | MUC-R |

| | | | | | | | | | | | | | | |
|---|---|---|---|---|---|---|---|---|---|---|---|---|---|---|
| L | T | A | D | I | V | A | A | Y | V | S | N | H | V | V | WT-ROS |
| L | T | A | D | I | V | A | A | Y | V | S | N | H | V | V | SYNROS |
| L | T | A | D | I | V | A | A | Y | V | S | N | H | V | V | ROS-R |
| L | T | A | D | I | V | A | A | Y | V | S | N | H | V | V | ROS-AR |
| L | T | A | E | I | V | A | A | Y | V | S | N | H | V | V | MUC-R |

| | | | | | | | | | | | | | | |
|---|---|---|---|---|---|---|---|---|---|---|---|---|---|---|
| P | V | T | E | L | P | G | L | I | S | D | V | H | T | A | WT-ROS |
| P | V | T | E | L | P | G | L | I | S | D | V | H | T | A | SYNROS |
| P | V | S | D | L | A | N | L | I | S | D | V | H | S | A | ROS-R |
| P | V | T | E | L | P | N | L | I | S | D | V | H | T | A | ROS-AR |
| P | V | <u>A</u> | E | L | <u>P</u> | <u>T</u> | L | I | <u>A</u> | D | V | H | <u>S</u> | A | MUC-R |

| | | | | | | | | | | | | | | |
|---|---|---|---|---|---|---|---|---|---|---|---|---|---|---|
| L | S | G | T | S | A | P | A | S | V | A | V | N | V | E | WT-ROS |
| L | S | G | T | S | A | P | A | S | V | A | V | N | V | E | SYNROS |
| L | S | N | T | S | V | P | Q | P | A | A | A | V | V | E | ROS-R |
| L | S | N | T | S | A | P | Q | S | V | A | V | N | V | E | ROS-AR |
| L | <u>N</u> | <u>N</u> | T | <u>T</u> | <u>A</u> | P | <u>A</u> | <u>P</u> | <u>V</u> | <u>V</u> | <u>V</u> | <u>P</u> | V | E | MUC-R |

| | | | | | | | | | | | | | | |
|---|---|---|---|---|---|---|---|---|---|---|---|---|---|---|
| K | Q | K | P | A | V | S | V | R | K | S | V | Q | D | D | WT-ROS |
| K | Q | K | P | A | V | S | V | R | K | S | V | Q | D | D | SYNROS |
| K | Q | K | P | A | V | S | V | R | K | S | V | Q | D | E | ROS-R |
| K | Q | K | P | A | V | S | V | R | K | S | V | Q | D | D | ROS-AR |
| K | <u>P</u> | K | P | A | V | S | V | R | K | S | V | Q | D | <u>D</u> | MUC-R |

| | | | | | | | | | | | | | | |
|---|---|---|---|---|---|---|---|---|---|---|---|---|---|---|
| H | I | V | C | L | E | C | G | G | S | F | K | S | L | K | WT-ROS |
| H | I | V | C | L | E | C | G | G | S | F | K | S | L | K | SYNROS |
| Q | I | T | C | L | E | C | G | G | N | F | K | S | L | K | ROS-R |
| H | I | V | C | L | E | C | G | G | S | F | K | S | L | K | ROS-AR |
| Q | I | T | C | L | E | C | G | G | T | F | K | S | L | K | MUC-R |

| | | | | | | | | | | | | | | |
|---|---|---|---|---|---|---|---|---|---|---|---|---|---|---|
| R | H | L | T | T | H | H | S | M | T | P | E | E | Y | R | WT-ROS |
| R | H | L | T | T | H | H | S | M | T | P | E | E | Y | R | SYNROS |
| R | H | L | M | T | H | H | S | L | S | P | E | E | Y | R | ROS-R |
| R | H | L | T | T | H | H | S | M | T | P | E | E | Y | R | ROS-AR |
| R | H | L | M | T | H | H | <u>N</u> | L | S | P | E | E | Y | R | MUC-R |

| | | | | | | | | | | | | | | |
|---|---|---|---|---|---|---|---|---|---|---|---|---|---|---|
| E | K | W | D | L | P | V | D | Y | P | M | V | A | P | A | WT-ROS |
| E | K | W | D | L | P | V | D | Y | P | M | V | A | P | A | SYNROS |
| E | K | W | D | L | P | T | D | Y | P | M | V | A | P | A | ROS-R |
| E | K | W | D | L | Q | V | D | Y | P | M | V | A | P | A | ROS-AR |
| D | K | W | D | L | P | A | D | Y | P | M | V | A | P | A | MUC-R |

| | | | | | | | | | | | | | | |
|---|---|---|---|---|---|---|---|---|---|---|---|---|---|---|
| Y | A | E | A | R | S | R | L | A | K | E | M | G | L | G | WT-ROS |
| Y | A | E | A | R | S | R | L | A | K | E | M | G | L | G | SYNROS |
| Y | A | E | A | R | S | R | L | A | K | E | M | G | L | G | ROS-R |
| Y | A | E | A | R | S | R | L | A | K | E | M | G | L | G | ROS-AR |
| Y | A | E | A | R | S | R | L | A | K | E | M | G | L | G | MUC-AR |

| | | | | | | | | | | | | | |
|---|---|---|---|---|---|---|---|---|---|---|---|---|---|
| Q | R | R | K | A | N | R | | | | | | | | WT-ROS |
| Q | R | R | K | A | N | R | P | K | K | R | K | V | | SYNROS |
| Q | R | R | K | A | N | R | G | | | | | | | ROS-R |
| Q | R | R | K | A | N | R | | | | | | | | ROS-AR |
| Q | R | R | K | R | G | R | K | | | | | | | MUC-AR |

FIGURE 1(A)

GCGGATCCCC GGGTATGACT GAGACTGCTT ACGGTAACGC
TCAGGATCTT CTTGTTGAGC TTACTGCTGA TATCGTTGCT
GCTTACGTTT CTAACCACGT TGTTCCTGTT ACTGAGCTTC
CTGGACTTAT CTCTGATGTT CATACTGCAC TTTCTGGAAC
ATCTGCTCCT GCTTCTGTTG CTGTTAACGT TGAGAAGCAG
AAGCCTGCTG TTTCTGTTCG TAAGTCTGTT CAGGATGATC
ATATCGTTTG TTTGGAGTGT GGTGGTTCTT TCAAGTCTCT
CAAGCGTCAC CTTACTACTC ATCACTCTAT GACTCCAGAG
GAGTATAGAG AGAAGTGGGA TCTTCCTGTT GATTACCCTA
TGGTTGCTCC TGCTTACGCT GAGGCTCGTT CTCGTCTCGC
TAAGGAGATG GGTCTCGGTC AGCGTCGTAA GGCTAACCGT
CCAAAAAAGA AGCGTAAGGT CTGAGAGCTC GC

FIGURE 1(B)

```
  M    T    E    T    A    Y    G    N    A    Q    D    L    L    V    E
 ATG  ACN  GAR  ACN  GCN  TAY  GGN  AAY  GCN  CAR  GAY  YTN  YTN  GTN  GAR

L    T    A    D    I    V    A    A    Y    V    S    N    H    V    V
 YTN  ACN  GCN  GAY  ATH  GTN  GCN  GCN  TAY  GTN  WSN  AAY  CAY  GTN  GTN

P    V    T    E    L    P    G    L    I    S    D    V    H    T    A
 CCN  GTN  ACN  GAR  YTN  CCN  GGN  YTN  ATH  WSN  GAY  GTN  CAY  ACN  GCN

L    S    G    T    S    A    P    A    S    V    A    V    N    V    E
 YTN  WSN  GGN  ACN  WSN  GCN  CCN  GCN  WSN  GTN  GCN  GTN  AAY  GTN  GAR

K    Q    K    P    A    V    S    V    R    K    S    V    Q    D    D
 AAR  CAR  AAR  CCN  GCN  GTN  WSN  GTN  MGN  AAR  WSN  GTN  CAR  GAY  GAY

H    I    V    C    L    E    C    G    G    S    F    K    S    L    K
 CAY  ATH  GTN  TGY  YTN  GAR  TGY  GGN  GGN  WSN  TTY  AAR  WSN  YTN  AAR

R    H    L    T    T    H    H    S    M    T    P    E    E    Y    R
 MGN  CAY  YTN  ACN  ACN  CAY  CAY  WSN  ATG  ACN  CCN  GAR  GAR  TAY  MGN

E    K    W    D    L    P    V    D    Y    P    M    V    A    P    A
 GAR  AAR  TGG  GAY  YTN  CCN  GTN  GAY  TAY  CCN  ATG  GTN  GCN  CCN  GCN

Y    A    E    A    R    S    R    L    A    K    E    M    G    L    G
 TAY  GCN  GAR  GCN  MGN  WSN  MGN  YTN  GCN  AAR  GAR  ATG  GGN  YTN  GGN

Q    R    R    K    A    N    R    P    K    K    K    R    K    V
 CAR  MGN  MGN  AAR  GCN  AAY  MGN  CCN  AAR  AAR  AAR  MGN  AAR  GTN
```

FIGURE 1(C)

ROS Inverted Repeat
DNA Binding Sites(Operator sequences)

TATATTTCAA-TTTTA-TTGTAATATA
*virC/virD*
\* \* \* \*   \* \*   \* \*   \*   \* \* \*     \* \* \*         \* \*
TATAATTAAAATATTACTGTCGCATT   *ipt*

FIGURE 1 (D)

Comparison of ROS DNA Binding Site (Operator) Sequences

| | |
|---|---|
| *VirC/VirD* | TATATTTCAA |
| | TATATTACAA |
| *ipt* | TATAATTAAA |
| | AATGCGACAG |
| | TATAHTtCAA |
| | a  g gaa g |
| Consensus | WATDHWKMAR |

Southern blot of DNA from p74-101 T1 plants.
HindIII digests probed with NPTII

Western blot analysis of total protein from T12 plants probed with ROS antibody

Columbia wt pBI121 p74-501 buffer

Repressor Construct

SEQUENCE LISTING

```
<160> NUMBER OF SEQ ID NOS: 45

<210> SEQ ID NO 1
<211> LENGTH: 429
<212> TYPE: DNA
<213> ORGANISM: Agrobacterium tumefaciens

<400> SEQUENCE: 1
atgacggaaa ctgcatacgg taacgcccag gatctgctgg tcgaactgac ggcggatatt      60
gtggctgcct atgttagcaa ccacgtcgtt ccggtaactg agcttcccgg ccttatttcg     120
gatgttcata cggcactcag cggaacatcg gcaccggcat cggtggcggt caatgttgaa     180
aagcagaagc ctgctgtgtc ggttcgcaag tcggttcagg acgatcatat cgtctgtttg     240
gaatgtggtg gctcgttcaa gtcgctcaaa cgccacctga cgacgcatca cagcatgacg     300
ccggaagaat atcgcgaaaa atgggatctg ccggtcgatt atccgatggt tgctcccgcc     360
tatgccgaag cccgttcgcg gctcgccaag gaaatgggtc tcggtcagcg ccgcaaggcg     420
aaccgttga                                                             429

<210> SEQ ID NO 2
<211> LENGTH: 458
<212> TYPE: DNA
<213> ORGANISM: Artificial
<220> FEATURE:
<223> OTHER INFORMATION: synthetic ROS optimized for plant codon usage
      and encoding fusion of ROS and nuclear localization signa

<400> SEQUENCE: 2
atgactgaga ctgcttacgg taacgctcag gatcttcttg ttgagcttac tgctgatatc      60
gttgctgctt acgtttctaa ccacgttgtt cctgttactg agcttcctgg acttatctct     120
gatgttcata ctgcactttc tggaacatct gctcctgctt ctgttgctgt taacgttgag     180
aagcagaagc ctgctgtttc tgttcgtaag tctgttcagg atgatcatat cgtttgtttg     240
gagtgtggtg gttctttcaa gtctctcaag cgtcacctta ctactcatca ctctatgact     300
ccagaggagt atagagagaa gtgggatctt cctgttgatt accctatggt tgctcctgct     360
tacgctgagg ctcgttctcg tctcgctaag gagatgggtc tcggtcagcg tcgtaaggct     420
aaccgtccaa aaaagaagcg taaggtctga gagctcgc                             458

<210> SEQ ID NO 3
<211> LENGTH: 447
<212> TYPE: DNA
<213> ORGANISM: Artificial
<220> FEATURE:
<223> OTHER INFORMATION: ROS consensus sequence
<220> FEATURE:
<221> NAME/KEY: misc_feature
<222> LOCATION: (1)..(447)
```

-continued

<223> OTHER INFORMATION: n is A or T or G or C
<220> FEATURE:
<221> NAME/KEY: misc_feature
<222> LOCATION: (1)..(447)
<223> OTHER INFORMATION: h is a or c or t/u
<220> FEATURE:
<221> NAME/KEY: misc_feature
<222> LOCATION: (1)..(447)
<223> OTHER INFORMATION: m is a or c
<220> FEATURE:
<221> NAME/KEY: misc_feature
<222> LOCATION: (1)..(447)
<223> OTHER INFORMATION: r is G or A
<220> FEATURE:
<221> NAME/KEY: misc_feature
<222> LOCATION: (1)..(447)
<223> OTHER INFORMATION: y is t/u or c
<220> FEATURE:
<221> NAME/KEY: misc_feature
<222> LOCATION: (1)..(447)
<223> OTHER INFORMATION: w is a or t/u

<400> SEQUENCE: 3
atgacngara cngcntaygg naaygcncar gayytnytng tngarytnac ngcngayath 60
gtngcngcnt aygtnwsnaa ycaygtngtn ccngtnacng arytnccngg nytnathwsn 120
gaygtncaya cngcnytnws nggnacnwsn gcnccngcnw sngtngcngt naaygtngar 180
aarcaraarc cngcngtnws ngtnmgnaar wsngtncarg aygaycayat hgtntgyytn 240
gartgyggng gnwsnttyaa rwsnytnaar mgncayytna cnacncayca ywsnatgacn 300
ccngargart aymgngaraa rtgggayytn ccngtngayt ayccnatggt ngcnccngcn 360
taygcngarg cnmgnwsnmg nytngcnaar garatgggny tnggncarmg nmgnaargcn 420
aaymgnccna araaraarmg naargtn 447

<210> SEQ ID NO 4
<211> LENGTH: 27
<212> TYPE: DNA
<213> ORGANISM: Artificial
<220> FEATURE:
<223> OTHER INFORMATION: sense primer for amplifying ROS coding region

<400> SEQUENCE: 4
gcggatccga tgacggaaac tgcatac 27

<210> SEQ ID NO 5
<211> LENGTH: 25
<212> TYPE: DNA
<213> ORGANISM: Artificial
<220> FEATURE:
<223> OTHER INFORMATION: antisense primer for amplifying ROS coding region

<400> SEQUENCE: 5
gcaagcttca acggttcgcc ttgcg 25

<210> SEQ ID NO 6
<211> LENGTH: 36
<212> TYPE: DNA
<213> ORGANISM: Artificial
<220> FEATURE:
<223> OTHER INFORMATION: sense primer for amplifying tms2 promoter

<400> SEQUENCE: 6
tgcggatgca taagcttgct gacattgcta gaaaag 36

<210> SEQ ID NO 7

```
<211> LENGTH: 26
<212> TYPE: DNA
<213> ORGANISM: Artificial
<220> FEATURE:
<223> OTHER INFORMATION: antisense primer for amplifying tms2 promoter

<400> SEQUENCE: 7
cggggatcct ttcagggcca tttcag                                          26

<210> SEQ ID NO 8
<211> LENGTH: 25
<212> TYPE: DNA
<213> ORGANISM: Artificial
<220> FEATURE:
<223> OTHER INFORMATION: ROS operator sequence

<400> SEQUENCE: 8
tatatttcaa ttttattgta atata                                           25

<210> SEQ ID NO 9
<211> LENGTH: 109
<212> TYPE: DNA
<213> ORGANISM: Artificial
<220> FEATURE:
<223> OTHER INFORMATION: ROS-OPDS oligo for p74-315 construct

<400> SEQUENCE: 9
atctccactg acgtaaggga tgacgcacaa tcccactatc cttcgcaaga cccttcctct     60
atataatata tttcaatttt attgtaatat aacacggggg actctagag              109

<210> SEQ ID NO 10
<211> LENGTH: 113
<212> TYPE: DNA
<213> ORGANISM: Artificial
<220> FEATURE:
<223> OTHER INFORMATION: ROS-OPDA oligo for p74-315 construct

<400> SEQUENCE: 10
gatcctctag agtcccccgt gttatattac aataaaattg aaatatatta tagaggaa       60 gggtcttgcg aaggatagtg ggattgtgcg tcatccctta cgtcagtgga gat           113

<210> SEQ ID NO 11
<211> LENGTH: 107
<212> TYPE: DNA
<213> ORGANISM: Artificial
<220> FEATURE:
<223> OTHER INFORMATION: ROS-OPUS oligo for p74-316 construct

<400> SEQUENCE: 11
atctccactg acgtaaggga tgacgcacaa tctatatttc aatttttattg taatatacta    60 tataaggaag ttcatttcat ttggagagaa cacgggggac tctagag                 107

<210> SEQ ID NO 12
<211> LENGTH: 111
<212> TYPE: DNA
<213> ORGANISM: Artificial
<220> FEATURE:
<223> OTHER INFORMATION: ROS-OPUA oligo for p74-316 construct

<400> SEQUENCE: 12
gatcctctag agtcccccgt gttctctcca aatgaaatga acttccttat atagtatatt     60
acaataaaat tgaaatatag attgtgcgtc atcccttacg tcagtggaga t             111
```

<210> SEQ ID NO 13
<211> LENGTH: 108
<212> TYPE: DNA
<213> ORGANISM: Artificial
<220> FEATURE:
<223> OTHER INFORMATION: ROS-OPPS oligo for p74-309 construct

<400> SEQUENCE: 13
atctccactg acgtaaggga tgacgcacaa tctatatttc aatttattg taatatacta      60 tataatatat ttcaatttta ttgtaatata acacggggga ctctagag               108

<210> SEQ ID NO 14
<211> LENGTH: 112
<212> TYPE: DNA
<213> ORGANISM: Artificial
<220> FEATURE:
<223> OTHER INFORMATION: ROS-OPPA oligo for p74-309 construct

<400> SEQUENCE: 14
gatcctctag agtccccgt gttatattac aataaaattg aaatatatta tatagtatat      60
tacaataaaa ttgaaatata gattgtgcgt catcccttac gtcagtggag at           112

<210> SEQ ID NO 15
<211> LENGTH: 59
<212> TYPE: DNA
<213> ORGANISM: Artificial
<220> FEATURE:
<223> OTHER INFORMATION: ROS-OP1 oligo for p76-508 construct

<400> SEQUENCE: 15
gatcctatat ttcaatttta ttgtaatata gctatatttc aatttattg taatataat      59

<210> SEQ ID NO 16
<211> LENGTH: 57
<212> TYPE: DNA
<213> ORGANISM: Artificial
<220> FEATURE:
<223> OTHER INFORMATION: ROS-OP2 oligo for p76-508 construct

<400> SEQUENCE: 16
cgattatatt acaataaaat tgaaatatag ctatattaca ataaaattga aatatag        57

<210> SEQ ID NO 17
<211> LENGTH: 24
<212> TYPE: DNA
<213> ORGANISM: Artificial
<220> FEATURE:
<223> OTHER INFORMATION: sense primer for amplifying Actin2 promoter

<400> SEQUENCE: 17
aagcttatgt atgcaagagt cagc                                             24

<210> SEQ ID NO 18
<211> LENGTH: 24
<212> TYPE: DNA
<213> ORGANISM: Artificial
<220> FEATURE:
<223> OTHER INFORMATION: antisense primer for amplifying Actin2 promoter

<400> SEQUENCE: 18
ttgactagta tcagcctcag ccat                                             24

<210> SEQ ID NO 19
<211> LENGTH: 27
<212> TYPE: DNA

```
<213> ORGANISM: Artificial
<220> FEATURE:
<223> OTHER INFORMATION: ROS operator sequence in ipt gene

<400> SEQUENCE: 19
tataattaaa atattaactg tcgcatt                                              27

<210> SEQ ID NO 20
<211> LENGTH: 10
<212> TYPE: DNA
<213> ORGANISM: Artificial
<220> FEATURE:
<223> OTHER INFORMATION: consensus ROS operator sequence

<400> SEQUENCE: 20 watdhwkmar                                                                 10

<210> SEQ ID NO 21
<211> LENGTH: 104
<212> TYPE: PRT
<213> ORGANISM: Agrobacterium radiobacter

<400> SEQUENCE: 21

Met Thr Thr Ala Tyr Gly Asn Ala Asp Val Thr Ala Asp Val Ala Ala
1               5                   10                  15

Tyr Val Ser Asn His Val Val Thr Gly Ser Asp Val His Thr Ala
            20                  25                  30

Ser Gly Thr Ser Ala Ala Ser Val Ala Val Asn Val Lys Lys Ala Val
        35                  40                  45

Ser Val Arg Lys Ser Val Asp Asp His Val Cys Cys Gly Gly Ser Lys
    50                  55                  60

Ser Lys Arg His Thr Thr His His Ser Met Thr Tyr Arg Lys Trp Asp
65                  70                  75                  80

Val Asp Tyr Met Val Ala Ala Tyr Ala Ala Arg Ser Arg Ala Lys Met
                85                  90                  95

Gly Gly Arg Arg Lys Ala Asn Arg
            100

<210> SEQ ID NO 22
<211> LENGTH: 138
<212> TYPE: DNA
<213> ORGANISM: Artificial
<220> FEATURE:
<223> OTHER INFORMATION: p74-315 sequence from EcoRV site to ATG codon
      of GUS

<400> SEQUENCE: 22
gatatctcca ctgacgtaag ggatgacgca caatcccact atccttcgca agacccttcc         60
tctatataat atatttcaat tttattgtaa tataacacgg gggactctag aggatccccg        120
ggtggtcagt cccttatg                                                      138

<210> SEQ ID NO 23
<211> LENGTH: 136
<212> TYPE: DNA
<213> ORGANISM: Artificial
<220> FEATURE:
<223> OTHER INFORMATION: p74-316 sequence from EcoRV site to ATG codon
      of GUS

<400> SEQUENCE: 23
gatatctcca ctgacgtaag ggatgacgca caatctatat ttcaatttta ttgtaatata         60
```

```
ctatataagg aagttcattt catttggaga gaacacgggg gactctagag gatccccggg    120
tggtcagtcc cttatg                                                    136

<210> SEQ ID NO 24
<211> LENGTH: 137
<212> TYPE: DNA
<213> ORGANISM: Artificial
<220> FEATURE:
<223> OTHER INFORMATION: p74-309 sequence from EcoRV site to ATG codon
      of GUS

<400> SEQUENCE: 24
gatatctcca ctgacgtaag ggatgacgca caatctatat ttcaatttta ttgtaatata    60
ctatataata tatttcaatt ttattgtaat ataacacggg ggactctaga ggatccccgg    120
gtggtcagtc ccttatg                                                   137

<210> SEQ ID NO 25
<211> LENGTH: 237
<212> TYPE: DNA
<213> ORGANISM: Artificial
<220> FEATURE:
<223> OTHER INFORMATION: p74-118 sequence from EcoRV site to ATG codon
      of GUS

<400> SEQUENCE: 25
gatatctcca ctgacgtaag ggatgacgca caatcccact atccttcgca agacccttcc    60
tctatataat atatttcaat tttattgtaa tataacacgg gggactctag aggatcctat    120
atttcaattt tattgtaata tagctatatt tcaattttat tgtaatataa tcgatttcga    180
acccggggta ccgaattcct cgagtctaga ggatccccgg gtggtcagtc ccttatg      237

<210> SEQ ID NO 26
<211> LENGTH: 142
<212> TYPE: PRT
<213> ORGANISM: Agrobacterium tumefaciens

<400> SEQUENCE: 26

Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Pro Val
            20                  25                  30

Thr Glu Leu Pro Gly Leu Ile Ser Asp Val His Thr Ala Leu Ser Gly
        35                  40                  45

Thr Ser Ala Pro Ala Ser Val Ala Val Asn Val Glu Lys Gln Lys Pro
    50                  55                  60

Ala Val Ser Val Arg Lys Ser Val Gln Asp Asp His Ile Val Cys Leu
65                  70                  75                  80

Glu Cys Gly Gly Ser Phe Lys Ser Leu Lys Arg His Leu Thr Thr His
                85                  90                  95

His Ser Met Thr Pro Glu Glu Tyr Arg Glu Lys Trp Asp Leu Pro Val
            100                 105                 110

Asp Tyr Pro Met Val Ala Pro Ala Tyr Ala Glu Ala Arg Ser Arg Leu
        115                 120                 125

Ala Lys Glu Met Gly Leu Gly Gln Arg Arg Lys Ala Asn Arg
    130                 135                 140

<210> SEQ ID NO 27
<211> LENGTH: 149
<212> TYPE: PRT
```

<213> ORGANISM: Artificial
<220> FEATURE:
<223> OTHER INFORMATION: synthetic-ROS fused to nuclear localization
     signal

<400> SEQUENCE: 27

Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Val Pro Val
            20                  25                  30

Thr Glu Leu Pro Gly Leu Ile Ser Asp Val His Thr Ala Leu Ser Gly
        35                  40                  45

Thr Ser Ala Pro Ala Ser Val Ala Val Asn Val Glu Lys Gln Lys Pro
    50                  55                  60

Ala Val Ser Val Arg Lys Ser Val Gln Asp His Ile Val Cys Leu
65                  70                  75                  80

Glu Cys Gly Gly Ser Phe Lys Ser Leu Lys Arg His Leu Thr Thr His
                85                  90                  95

His Ser Met Thr Pro Glu Glu Tyr Arg Glu Lys Trp Asp Leu Pro Val
            100                 105                 110

Asp Tyr Pro Met Val Ala Pro Ala Tyr Ala Glu Ala Arg Ser Arg Leu
        115                 120                 125

Ala Lys Glu Met Gly Leu Gly Gln Arg Arg Lys Ala Asn Arg Pro Lys
    130                 135                 140

Lys Lys Arg Lys Val
145

<210> SEQ ID NO 28
<211> LENGTH: 143
<212> TYPE: PRT
<213> ORGANISM: rhizobium elti

<400> SEQUENCE: 28

Met Thr Asp Met Ala Thr Gly Asn Ala Pro Glu Leu Leu Val Glu Leu
1               5                   10                  15

Thr Ala Asp Ile Val Ala Ala Tyr Val Ser Asn His Val Val Pro Val
            20                  25                  30

Ser Asp Leu Ala Asn Leu Ile Ser Asp Val His Ser Ala Leu Ser Asn
        35                  40                  45

Thr Ser Val Pro Gln Pro Ala Ala Val Val Glu Lys Gln Lys Pro
    50                  55                  60

Ala Val Ser Val Arg Lys Ser Val Gln Asp Glu Gln Ile Thr Cys Leu
65                  70                  75                  80

Glu Cys Gly Gly Asn Phe Lys Ser Leu Lys Arg His Leu Met Thr His
                85                  90                  95

His Ser Leu Ser Pro Glu Glu Tyr Arg Glu Lys Trp Asp Leu Pro Thr
            100                 105                 110

Asp Tyr Pro Met Val Ala Pro Ala Tyr Ala Glu Ala Arg Ser Arg Leu
        115                 120                 125

Ala Lys Glu Met Gly Leu Gly Gln Arg Arg Lys Arg Gly Arg Gly
    130                 135                 140

<210> SEQ ID NO 29
<211> LENGTH: 142
<212> TYPE: PRT
<213> ORGANISM: agrobacterium radiobacter

<400> SEQUENCE: 29

```
Met Thr Glu Thr Ala Tyr Gly Asn Ala Gln Asp Leu Leu Val Glu Leu
1               5                   10                  15

Thr Ala Asp Ile Val Ala Ala Tyr Val Ser Asn His Val Pro Val
            20                  25                  30

Thr Glu Leu Pro Gly Leu Ile Ser Asp Val His Thr Ala Leu Ser Gly
            35                  40                  45

Thr Ser Ala Pro Ala Ser Val Ala Val Asn Val Glu Lys Gln Lys Pro
    50                  55                  60

Ala Val Ser Val Arg Lys Ser Val Gln Asp Asp His Ile Val Cys Leu
65                  70                  75                  80

Glu Cys Gly Gly Ser Phe Lys Ser Leu Lys Arg His Leu Thr Thr His
                85                  90                  95

His Ser Met Thr Pro Glu Glu Tyr Arg Glu Lys Trp Asp Leu Gln Val
            100                 105                 110

Asp Tyr Pro Met Val Ala Pro Ala Tyr Ala Glu Ala Arg Ser Arg Leu
            115                 120                 125

Ala Lys Glu Met Gly Leu Gly Gln Arg Arg Lys Ala Asn Arg
    130                 135                 140
```

```
<210> SEQ ID NO 30
<211> LENGTH: 143
<212> TYPE: PRT
<213> ORGANISM: rhizobium meliloti

<400> SEQUENCE: 30
```

```
Met Thr Glu Thr Ser Leu Gly Thr Ser Asn Glu Leu Leu Val Glu Leu
1               5                   10                  15

Thr Ala Glu Ile Val Ala Ala Tyr Val Ser Asn His Val Pro Val
            20                  25                  30

Ala Glu Leu Pro Thr Leu Ile Ala Asp Val His Ser Ala Leu Asn Asn
            35                  40                  45

Thr Thr Ala Pro Ala Pro Val Val Pro Val Glu Lys Pro Lys Pro
    50                  55                  60

Ala Val Ser Val Arg Lys Ser Val Gln Asp Asp Gln Ile Thr Cys Leu
65                  70                  75                  80

Glu Cys Gly Gly Thr Phe Lys Ser Leu Lys Arg His Leu Met Thr His
                85                  90                  95

His Asn Leu Ser Pro Glu Glu Tyr Arg Asp Lys Trp Asp Leu Pro Ala
            100                 105                 110

Asp Tyr Pro Met Val Ala Pro Ala Tyr Ala Glu Ala Arg Ser Arg Leu
            115                 120                 125

Ala Lys Glu Met Gly Leu Gly Gln Arg Arg Lys Arg Gly Lys
    130                 135                 140
```

```
<210> SEQ ID NO 31
<211> LENGTH: 16
<212> TYPE: PRT
<213> ORGANISM: Arabidopsis sp.

<400> SEQUENCE: 31
```

```
Arg Ile Glu Asn Thr Thr Asn Arg Gln Val Thr Phe Cys Lys Arg Arg
1               5                   10                  15
```

```
<210> SEQ ID NO 32
<211> LENGTH: 18
<212> TYPE: PRT
<213> ORGANISM: Nicotiana sp.
```

```
<400> SEQUENCE: 32

Arg Arg Leu Ala Gln Asn Arg Glu Ala Ala Arg Lys Ser Arg Leu Arg
1               5                   10                  15

Lys Lys

<210> SEQ ID NO 33
<211> LENGTH: 21
<212> TYPE: PRT
<213> ORGANISM: Nicotiana sp.

<400> SEQUENCE: 33

Lys Lys Arg Ala Arg Leu Val Arg Asn Arg Glu Ser Ala Gln Leu Ser
1               5                   10                  15

Arg Gln Arg Lys Lys
            20

<210> SEQ ID NO 34
<211> LENGTH: 18
<212> TYPE: PRT
<213> ORGANISM: Zea mays

<400> SEQUENCE: 34

Arg Lys Arg Lys Glu Ser Asn Arg Glu Ser Ala Arg Arg Ser Arg Tyr
1               5                   10                  15

Arg Lys

<210> SEQ ID NO 35
<211> LENGTH: 47
<212> TYPE: PRT
<213> ORGANISM: Unknown
<220> FEATURE:
<223> OTHER INFORMATION: potyvirus nuclear localization signal
<220> FEATURE:
<221> NAME/KEY: misc_feature
<222> LOCATION: (12)..(44)
<223> OTHER INFORMATION: where "Xaa" is unknown or other

<400> SEQUENCE: 35

Lys Lys Asn Gln Lys His Lys Leu Lys Ala Ala Met Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Lys Arg Lys
        35                  40                  45

<210> SEQ ID NO 36
<211> LENGTH: 17
<212> TYPE: PRT
<213> ORGANISM: xenopus

<400> SEQUENCE: 36

Lys Arg Pro Ala Ala Thr Lys Lys Ala Gly Gln Ala Lys Lys Lys Lys
1               5                   10                  15

Leu

<210> SEQ ID NO 37
<211> LENGTH: 17
<212> TYPE: PRT
<213> ORGANISM: xenopus

<400> SEQUENCE: 37
```

-continued

```
Lys Arg Ile Ala Pro Asp Ser Ala Ser Lys Val Pro Arg Lys Lys Thr
1               5                   10                  15

Arg

<210> SEQ ID NO 38
<211> LENGTH: 17
<212> TYPE: PRT
<213> ORGANISM: xenopus

<400> SEQUENCE: 38

Lys Arg Lys Thr Glu Glu Glu Ser Pro Leu Lys Asp Lys Asp Ala Lys
1               5                   10                  15

Lys

<210> SEQ ID NO 39
<211> LENGTH: 17
<212> TYPE: PRT
<213> ORGANISM: Mus sp./Rattus sp.

<400> SEQUENCE: 39

Arg Lys Cys Leu Gln Ala Gly Met Asn Leu Glu Ala Arg Lys Thr Lys
1               5                   10                  15

Lys

<210> SEQ ID NO 40
<211> LENGTH: 17
<212> TYPE: PRT
<213> ORGANISM: Homo sapiens

<400> SEQUENCE: 40

Arg Lys Cys Leu Gln Ala Gly Met Asn Leu Glu Ala Arg Lys Thr Lys
1               5                   10                  15

Lys

<210> SEQ ID NO 41
<211> LENGTH: 17
<212> TYPE: PRT
<213> ORGANISM: Homo sapiens

<400> SEQUENCE: 41

Arg Lys Cys Leu Gln Ala Gly Met Asn Leu Glu Ala Arg Lys Thr Lys
1               5                   10                  15

Lys

<210> SEQ ID NO 42
<211> LENGTH: 17
<212> TYPE: PRT
<213> ORGANISM: Gallus sp.

<400> SEQUENCE: 42

Arg Lys Cys Cys Gln Ala Gly Met Val Leu Gly Gly Arg Lys Phe Lys
1               5                   10                  15

Lys

<210> SEQ ID NO 43
<211> LENGTH: 17
<212> TYPE: PRT
<213> ORGANISM: Homo sapiens

<400> SEQUENCE: 43

Arg Lys Cys Tyr Glu Ala Gly Met Thr Leu Gly Ala Arg Lys Leu Lys
```

-continued

```
                1               5              10              15
Lys

<210> SEQ ID NO 44
<211> LENGTH: 17
<212> TYPE: PRT
<213> ORGANISM: Gallus sp.

<400> SEQUENCE: 44

Arg Arg Cys Phe Glu Val Arg Val Cys Ala Cys Pro Gly Arg Asp Arg
1               5                  10                  15

Lys

<210> SEQ ID NO 45
<211> LENGTH: 236
<212> TYPE: DNA
<213> ORGANISM: Artificial
<220> FEATURE:
<223> OTHER INFORMATION: p74-114 sequence from EcoRV to ATG codon of GUS

<400> SEQUENCE: 45
gatatctcca ctgacgtaag ggatgacgca caatctatat ttcaatttta ttgtaatata      60
ctatataata tatttcaatt ttattgtaat ataacacggg ggactctaga ggatcctata    120
tttcaatttt attgtaatat agctatattt caattttatt gtaatataat cgatttcgaa    180 cccgggtac cgaattcctc gagtctagag gatccccggg tggtcagtcc cttatg         236
```

REPRESSOR-MEDIATED REGULATION SYSTEM FOR CONTROL OF GENE EXPRESSION IN PLANTS

CROSS-REFERENCE TO RELATED APPLICATIONS

This application is a continuation of PCT international application number PCT/CA02/01807 filed Nov. 21, 2002 and published in English as WO 03/100063 on Dec. 4, 2003 and claims priority from PCT/CA02/00740 filed May 23, 2002, the disclosures of which are incorporated by reference in their entirety.

The present invention relates to the regulation of gene expression. More particularly, the present invention pertains to the control of gene expression of one or more nucleotide sequences of interest in transgenic plants using a repressor protein and corresponding operator sequences.

BACKGROUND OF THE INVENTION

Transgenic plants have been an integral component of advances made in agricultural biotechnology. They are necessary tools for the production of plants exhibiting desirable traits (e.g. herbicide and insect resistance, drought and cold tolerance), or producing products of nutritional or pharmaceutical importance. As the applications of transgenic plants become ever more sophisticated, it is becoming increasingly necessary to develop strategies to fine-tune the expression of introduced genes. The ability to tightly regulate the expression of transgenes is important to address many safety, regulatory and practical issues. To this end, it is necessary to develop tools and strategies to regulate the expression of transgenes in a predictable manner.

Several strategies have so far been employed to control plant gene/transgene expression. These include the use of regulated promoters, such as inducible or developmental promoters, whereby the expression of genes of interest is driven by promoters responsive to various regulatory factors (Gatz, 1997, Ann. Rev. Plant Physiol. Plant Mol. Biol., 48: 89). Other strategies involve co-suppression (Eisner et al., 1998, Ther. Appl. Genet:, 97: 801) or anti-sense technology (Kohno-Murase et al., 1994, Plant Mol. Biol., 26: 1115), whereby plants are transformed with genes, or fragments thereof, that are homologous to genes either in the sense or antisense orientations. Chimeric RNA-DNA oligonucleotides have also been used to block the expression of target genes in plants (Beetham et al., 1999, Proc. Natl. Acad. Sci. USA, 96: 8774; Zhu et al., 1999, Proc. Natl. Acad. Sci. USA, 96: 8768).

The ROS protein is encoded by the chromosomal gene, ROS, of *Agrobacterium tumefaciens*. In this organism, the ROS protein acts as a negative regulator for the expression of the Ti-plasmid-encoded VirC, VirD and IPT genes (Cooley et al., J. 1991, Bacteriol. 173: 2608-2616; Chou et al., 1998, Proc. Natl. Acad. Sci., 95: 5293; Archdeacon J et al. 2000, FEMS Microbiol Let. 187: 175-178; D'Souza-Ault M. R., 1993, J Bacteriol 175: 3486-3490). The ROS protein is a DNA binding protein that is able to bind a ROS operator sequence (D'Souza-Ault M. R., 1993, J Bacteriol 175: 3486-3490).

Analysis of the amino acid sequence of the ROS protein reveals that it has a DNA binding motif of the $C_2H_2$ zinc finger configuration (Chou et al., 1998, Proc. Natl. Acad. Sci., 95: 5293). Typical zinc fingers are characterised by the presence of two cysteine and two histidine residues joined together by the coordination of a single zinc ion. A stretch of amino acids forms a peptide loop, known as the zinc finger motif that is required for DNA binding. Zinc finger proteins represent a significant portion of proteins in eukaryotes, but are rare in prokaryotes. The zinc finger of the bacterial ROS protein varies from its counterparts in eukaryotes in that the ROS protein has only one zinc finger motif, while eukaryotic zinc finger proteins have multiple zinc finger motifs. In addition, there are 9 amino acid residues making up the peptide loop spacing the zinc finger motif in the ROS protein as compared to the 12 amino acids that make up the loops of zinc fingers of eukaryotic proteins.

There is no suggestion for the use of ROS repressor to regulate gene expression within plants. The present invention provides a method for the regulation of gene expression in plants using a nucleic acid sequence, or derivatives of thereof, that encode ROS.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the regulation of gene expression. More particularly, the present invention pertains to the control of gene expression of one or more nucleotide sequences of interest in transgenic plants using a repressor protein and corresponding operator sequences.

According to the present invention there is provided a method (A) for selectively controlling the transcription of a gene of interest, comprising:

i) producing a first plant comprising a first genetic construct, the first genetic construct comprising a first regulatory region operatively linked to a gene of interest and at least one repressor operator sequence capable of controlling the activity of the first regulatory region;

ii) producing a second plant comprising a second genetic construct, the second genetic construct comprising a second regulatory region in operative association with a nucleic the molecule, or a derivative thereof, encoding a repressor, the repressor exhibiting both repressor operator binding activity and repressor activity;

iii) crossing the first plant and the second plant to obtain progeny, the progeny comprising both the first genetic construct and the second genetic construct, and characterized in that the expression of the second genetic construct represses expression of the gene of interest.

It is preferred that the gene encoding the repressor is optimized for expression in the plant, and that the gene encodes a nuclear localization signal. Furthermore, it is preferred that the repressor is a ROS repressor, and the repressor operator sequence is a ROS operator sequence.

The present invention also embraces the above method (A), wherein the first and second regulatory regions are either the same or different and are selected from the group consisting of a constitutive promoter, an inducible promoter, a tissue specific promoter, and a developmental promoter.

The present invention further provides a method (B) for selectively controlling the transcription of a gene of interest in a plant, comprising:

i) introducing into the plant either separately, or within the same vector:

a) a first genetic construct comprising a nucleic acid molecule comprising a first regulatory region operatively linked to a gene of interest, and at least one ROS operator sequence capable of controlling the activity of the first regulatory region; and b) a second genetic construct comprising a second regulatory region in operative association with a nucleotide sequence encoding a ROS repressor, or a derivative thereof, said ROS repressor exhibiting ROS operator binding activity, ROS repressor activity or both ROS operator binding activity and ROS repressor activity, the second regulatory region comprises an inducible promoter, ii) growing the plant, and iii) inducing the activity of said inducible promoter so that expression of the second genetic construct produces the ROS repressor and represses expression of the gene of interest.

It is preferred that the gene encoding the repressor is optimized for expression in the plant, and that the gene encodes a nuclear localization signal. Furthermore, it is preferred that the repressor is a ROS repressor, and the repressor operator sequence is a ROS operator sequence.

The present invention embraces a method (C) for selectively controlling the transcription of a gene of interest in a plant, comprising:

i) introducing into the plant either separately, or within the same vector:

a) a first genetic construct comprising a nucleic acid molecule comprising a first regulatory region operatively linked to a gene of interest, and at least one ROS operator sequence capable of controlling the activity of the first regulatory region; and b) a second genetic construct comprising a second regulatory region in operative association with a nucleotide sequence encoding a ROS repressor, or a derivative thereof, said ROS repressor exhibiting ROS operator binding activity, ROS repressor activity, or both ROS operator binding activity ROS repressor activity, the second regulatory region comprises a tissue specific promoter; and ii) growing said plant, so that expression of said second genetic construct produces said ROS repressor and represses expression of said gene of interest in a tissue specific manner.

It is preferred that the gene encoding the repressor is optimized for expression in the plant, and that the gene encodes a nuclear localization signal. Furthermore, it is preferred that the repressor is a ROS repressor, and the repressor operator sequence is a ROS operator sequence.

The present invention also provides a method (D) for selectively controlling the transcription of a gene of interest in a plant, comprising:

i) introducing into the plant either separately, or within the same vector:

a) a first genetic construct comprising a nucleic acid molecule comprising a first regulatory region operatively linked to a gene of interest, and at least one ROS operator sequence capable of controlling the activity of the first regulatory region; and b) a second genetic construct comprising a second regulatory region in operative association with a nucleotide sequence encoding a ROS repressor, or a derivative thereof, said ROS repressor exhibiting ROS operator binding activity, ROS repressor activity, or both ROS operator binding activity ROS repressor activity; second regulatory region comprises a promoter that is active at one or more specific developmental stages within the plant; and ii) growing the plant so that the activity of the promoter at one or more specific developmental stages within the plant results in expression of the second genetic construct thereby producing said ROS repressor, and represses expression of the gene of interest.

It is preferred that the gene encoding the repressor is optimized for expression in the plant, and that the gene encodes a nuclear localization signal. Furthermore, it is preferred that the repressor is a ROS repressor, and the repressor operator sequence is a ROS operator sequence.

The present invention is also directed to a nucleic acid molecule, or a derivative thereof, encoding a ROS repressor optimized for plant codon usage and exhibiting both ROS operator binding activity and ROS repressor activity. The nucleic acid molecule or a derivative thereof, maybe characterized as comprising one or more of the following properties:

a) comprising greater than 80% similarity with the nucleotide sequence of SEQ ID NO:2 or 3 as determined by use of the BLAST algorithm with the following. parameters: blastn; Database: nr; Expect 10; filter: low complexity; Alignment: pairwise; Word Size: 11;

b) hybridizing under stringent conditions with the nucleotide sequence of SEQ ID NO:2 or 3, comprising hybridizing for 16-20 hrs at 65° C. in 7% SDS, 1 mM EDTA, 0.5M $Na_2HPO_4$, pH 7.2, followed by washing in 5% SDS, 1 mM EDTA 40 mM $Na_2HPO_4$, pH 7.2 for 30 min, followed by washing in 1% SDS, 1 mM EDTA 40 mM $Na_2HPO_4$, pH 7.2 for 30 min;

c) comprising the nucleotide sequence of SEQ ID NO:2; and d) comprising the nucleotide sequence of SEQ ID NO:3.

Furthermore, the present invention relates to a genetic construct comprising a regulatory region in operative association with the nucleic acid molecule as defined above, and to a plant, or seed comprising the genetic construct.

The present invention also pertains to a nucleic acid molecule as defined above, further comprising a nuclear localization signal fused to the nucleic acid molecule, and to a genetic construct comprising a nuclear localization signal fused to the nucleic acid molecule as defined above. The present invention includes, a plant, or seed comprising the genetic construct as just defined.

The present invention further relates to a nucleic acid molecule comprising a regulatory region operatively linked to a gene of interest and at least one ROS operator sequence capable of controlling the activity of the regulatory region, wherein the regulatory region is functional in plants. Preferably, the at least one ROS operator sequence comprises the nucleotide sequence of SEQ ID NO:8. This invention also provides a genetic construct comprising the nucleic acid molecule as just defined, and to a plant comprising the genetic construct.

The present invention also pertains to a plant comprising a first genetic construct comprising a first nucleic acid molecule comprising a first regulatory region operatively linked to a gene of interest, and at least one ROS operator sequence capable of controlling the activity of the first regulatory region, and a second genetic construct comprising a second nucleic acid molecule, or a derivative thereof, encoding a ROS repressor optimized for plant codon usage and exhibiting ROS operator binding activity, ROS repressor activity, or both ROS operator binding activity ROS repressor activity.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows the nucleotide and deduced amino acid sequences of wild type ROS and a modified ROS of *Agrobacterium tumefaciens*. FIG. 1(A) shows the amino acid sequence alignment of known ROS repressors (SEQ ID NOs: 26,28,29,30), and a synthetic ROS (SEQ ID NO:27). The amino acid sequence 'PKKKRKV' at the carboxy end of synthetic ROS is one of several nuclear localization signals. FIG. 1(B) shows the nucleotide sequence of a synthetic ROS that had been optimized for plant codon usage containing a nuclear localization signal peptide (in italics). Optional restriction sites at the 5' end of the sequence are underlined (also see SEQ ID NO:2). FIG. 1(C) shows the consensus nucleotide (SEQ ID NO:3) and predicted amino acid sequence, of a composite ROS sequence comprising all possible nucleotide sequences that encode wild type ROS repressor, and the wild type ROS amino acid sequence. The amino acid sequence 'PKKKRKV' at the carboxy end represents a nuclear localization signal. Amino acids in bold identify the zinc finger motif.

Nucleotide codes are as follows: N=A or C or T or G; R=A or G; Y=C or T; M=A or C; K=T or G; S=C or G; W=A or T; H=A or T or C; B=T or C or G; D=A or T or G; V=A or C or G. FIG. 1(D) shows the nucleotide sequence of the DNA binding sites (operator sequences) of the virC/virD and ipt genes. FIG. 1(E) shows a consensus operator sequence derived from the virC/virD and ipt operator sequences (SEQ ID NO:20). This sequence comprises 10 nucleotides, however, only the first 9 nucleotides are required for binding ROS.

FIG. 2 displays the structure of various constructs in which the transcription of a modified ROS or wild type ROS nucleotide sequence is placed under control of various regulatory regions. The modified ROS nucleotide sequence is designated as 'synthetic ROS'.

FIG. 3 shows schematic representations of nucleotide constructs that place the expression of a gene of interest under the control a regulatory region, in this case a CaMV35S regulatory region, modified to contain a ROS operator site.

FIG. 4 shows a schematic representation of a nucleotide construct that places the expression of a gene of interest gene under the control of a regulatory region, in this case, the tms2 regulatory region that has been modified to contain ROS operator sites.

FIG. 5 shows a schematic representation of a nucleotide construct that places the expression of a gene of interest under the control of a regulatory region, in this case actin 2 regulatory region, that has been modified to contain ROS operator sites.

FIG. 6 shows Southern analysis of transgenic *Arabidopsis* plants.

FIG. 9A shows GUS activity in the ROS and GUS parents and the progeny obtained from the cross of the ROS and GUS parents. FIG. 9B shows Northern analysis of RNA obtained from ROS and GUS parents and the progeny of the cross between the ROS and GUS parents and probed with either a ROS or GUS probe. FIG. 9C shows Southern analysis of the progeny of the cross between the GUS and ROS parent plants, probed with either a GUS or ROS probe.

FIG. 10 shows several non-limiting examples of constructs of the present invention, that and referred to FIG. 11.

| Crosses | Constucts Female X male | Parental lines Female X male parent |
|---|---|---|
| Cross1(C1) | 74-316 X 74-101 | P1GUS X P1ROS |
| Cross2(C2) | 74-101 X 74-117 | P2ROS X P2GUS |
| Cross3(C3) | 74-118 X 74-101 | P3GUS X P3ROS |
| Cross4(C4) | 74-117 X 74-101 | P2GUS X P2ROS |
| Cross5(C5) | 74-313 X 74-501 | P5ROS X P5GUS |

Figure 11A:
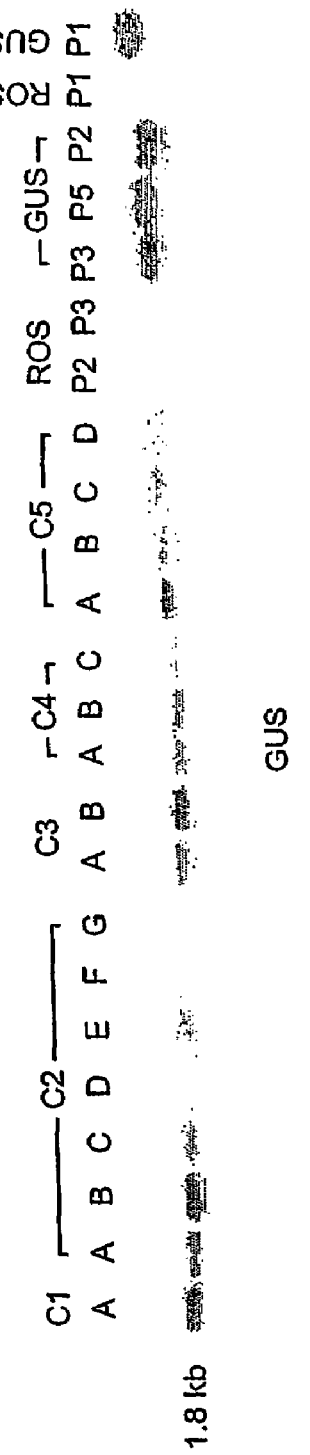
In FIGS. 11A-C, total RNA (~4.5g) was isolated from *Arabidopsis* parental lines comprising a first nucleotide sequence, expressing a gene of interest, in this case GUS (lanes marked GUS), a second nucleotide sequence, expressing synRos (lanes marked ROS), and crosses between various combinations of parental lines (C1-C5; see FIG. 10 for constructs) as follows.

Parental transgenic plants, and progeny arising from the crosses, were analyzed for GUS, using a GUS probe (FIG. 11A), and synROS, using a ROS probe (FIG. 11B), expression. FIG. 11C shows the loading of the RNA gel used for FIGS. 11A and B. FIG. 11D shows quantification of the densities of bands generated by Northern blot analysis of total RNA and probed with GUS as shown in FIG. 11A. B1 and B2 are blank (background) samples. Plant lines are as indicated in the Table above. Band intensity was calculated using Quantity One Software (Biorad).

Figure 12A:
Figure 12B:
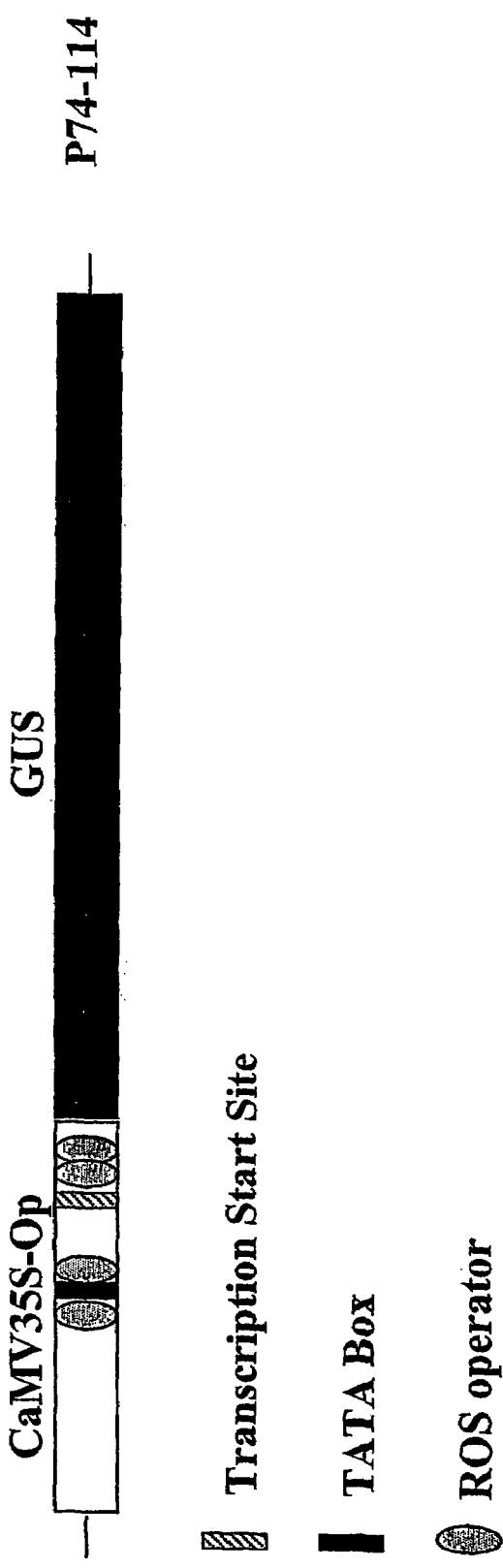

FIG. 12 shows non-limiting examples of a first nucleotide sequence and a second nucleotide sequence of the invention. FIG. 12A shows the structure of the p74-101 repressor construct (a second nucleotide sequence also described in FIG. 2D) in which an actin2 regulatory region is operatively linked to a protein coding region of synthetic ROS. FIG. 12B shows the structure of the p74-114 reporter construct (a first nucleotide sequence) in which a CaMV35S regulatory region, modified to contain 4 ROS operator sequences, is operatively linked to a protein encoding region of GUS. An operator sequence (OS) is shown as a filled oval with one OS upstream and three OS downstream of a TATA Box sequence.

Figure 13A:
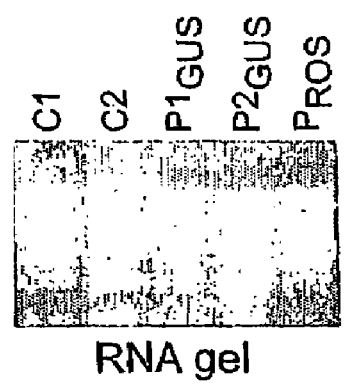
Figure 13B:
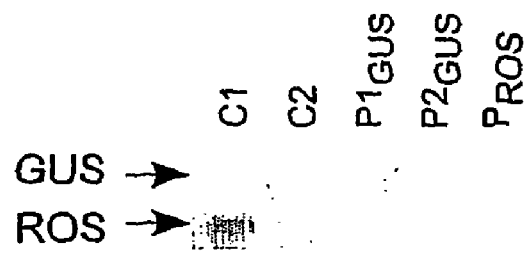
Figure 13C:
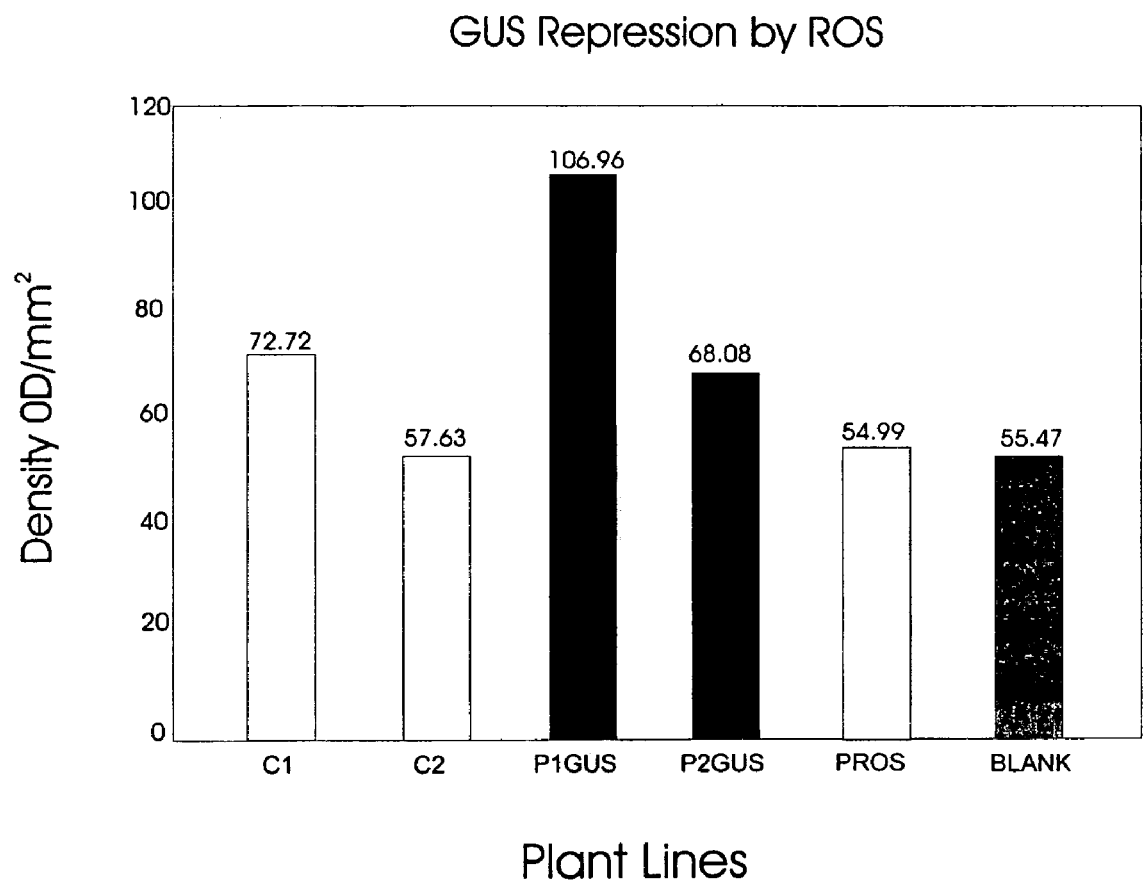

FIG. 13 shows Northern blot analysis of total RNA isolated from *Brassica napus* reporter/repressor crosses and parental lines. In FIGS. 13A-C transgenic *B. napus* plants were crossed and analyzed for expression levels of both GUS and ROS genes. The female parent is indicated first. Crosses performed are as follows: C1 and C2 are p74-114xp74-101. P1GUS is GUS parent plant for cross 1. P2GUS is GUS parent plant for cross2. PROS is ROS parent plant for crosses C1 and C2. FIG. 13A shows RNA loaded on a gel (approximately 4.5 ug of total RNA loaded per lane) prior to probing with GUS and synthetic ROS nucleic acid probes. FIG. 13B shows expression levels of crosses and parental lines probed with GUS (top) and synthetic ROS (bottom). FIG. 13C shows quantification of the densities of bands generated by northern blot analysis as shown in FIG. 13B. Plant lines are as indicated in FIGS. 13A and B. Band intensity was measured using Quantity One Software (Biorad).

DESCRIPTION OF PREFERRED EMBODIMENT

The present invention relates to the regulation of gene expression. More particularly, the present invention pertains to the control of gene expression of one or more nucleotide sequences of interest in transgenic plants using a repressor protein and corresponding operator sequences.

The following description is of a preferred embodiment by way of example only and without limitation to the combination of features necessary for carrying the invention into effect.

Gene repression can be used in applications such as metabolic engineering to produce plants that accumulate large amounts of certain intermediate compounds. Repression of gene expression can also be used for control of transgenes across generations, or production of F1 hybrid plants with seed characteristics that would be undesirable in the parental line, for example but not limited to, hyper-high oil, reduced fiber content low glucosinolate levels, reduced levels of phytotoxins, and the like. In the latter examples, low glucosinolate levels, or other phytotoxins, may be desired in seeds while higher concentrations of these compounds maybe required elsewhere, for example in the case of glucosinolates, within cotyledons, due to their role in plant defence. Another non-limiting example for the controlled regulation of a gene of interest during plant development is seed specific down regulation of sinapine biosynthesis, as for example in seeds of *Brasicca napus*. In many instances, transgene expression needs to be repressed only in certain plant organs/tissues or at certain stages of development. The methods as described herein may also be used to control the expression of a gene of interest that encodes a protein used to for plant selection purposes. For example, which is to be considered non-limiting, a gene of interest may encode a protein that is capable of metabolizing a compound from a non-toxic form to a toxic form thereby selectively removing plants that express the gene of interest.

The present invention is directed to a method of controlling gene expression using a repressor protein as a regulatory switch to repress the expression of a gene or coding region of interest, or repress the transcription of one, or more than one, selected nucleotide sequences by transforming a plant with one, or more than one, constructs comprising:

1) a first nucleotide sequence comprising a gene(or coding region) of interest operatively linked to a regulatory region comprising at least one repressor operator sequence that interacts with a repressor protein.

2) a second nucleotide sequence comprising a regulatory region in operative association with a nucleotide sequence encoding the repressor protein.

Preferably the repressor protein is ROS, and the repressor operator sequence is a ROS repressor operator sequence, for example but not limited to the ROS reporessor encoded by the nucleic acid sequence of SEQ ID NO:3.

These first and second nucleotide sequences may be placed within the same or within different vectors, genetic constructs, or nucleic acid molecules. When both constructs are expressed within the same plant, the expression of the repressor protein results in the down regulation in the expression of a gene (or coding region) of interest that is in operative association, or operatively linked, with an operator sequence that exhibits an affinity for the repressor protein. By "operatively association" or "operatively linked" it is meant that the particular sequences interact either directly or indirectly to carry out their intended function, such as mediation or modulation of gene expression. The interaction of operatively linked sequences may be mediated by proteins that in turn interact with the sequences, as described herein. A transcriptional regulatory region and a sequence of interest are "operably linked" when the sequences are functionally connected so as to permit transcription of the sequence of interest to be mediated or modulated by the transcriptional regulatory region.

By the term "expression" it is meant the production of a functional RNA, protein or both, from a gene or transgene.

By "repression of gene expression" it is meant the reduction in the level of mRNA, protein, or both mRNA and protein, encoded by a gene or nucleotide sequence of interest. Repression of gene expression may also arise as a result of the lack of production of full length RNA, for example mRNA, due to blocking migration of polymerase along a nucleic acid during transcription. A repression of gene expression may be a consequence of repressing, blocking or interrupting transcription.

By "repressor" or "repressor protein" it is meant a protein that exhibits the property of specifically binding to a corresponding operator sequence. An example of repressor protein, which is not to be considered limiting in any manner is the ROS repressor, or an analog or derivative thereof as defined herein. By "ROS repressor" it is meant any ROS repressor as known within the art. These include the ROS repressor as described herein, as well as other microbial ROS repressors, for example but not limited to ROSAR (*Agrobacterium radiobacter*; Brightwell et al., (1995) Mol. Plant Microbe Interact. 8: 747-754), MucR (*Rhizobium meliloti*; Keller M et al., (1995) Mol. Plant Microbe Interact. 8: 267-277), and ROSR (*Rhizobium elti*; Bittinger et al., (1997) Mol. Plant Microbe Interact. 10: 180-186; also see Cooley et al. 1991, J. Bacteriol. 173:2608-2616; Chou et al., 1998, Proc. Natl. Acad. Sci., 95: 5293; Archdeacon J et al. 2000, FEMS Microbiol Let. 187: 175-178; D'Souza-Ault M. R., 1993, J Bacteriol 175: 3486-3490; all of which are incorporated herein by reference). Examples of a ROS repressor, which are not to be considered limiting, are provide in FIGS. 1(A) to (C) and (SEQ ID NO's: 1-3 and 21). An analog, or a derivative, of a repressor protein maybe any protein that exhibits the property of binding an operator sequence, for example which is not to be considered limiting in any manner, a fusion protein comprising an operator binding sequence fused to a second protein. The second protein may be any protein, including:

- a protein having an activity that regulates gene expression when bound to the operator sequence, for example but not limited to histone deacetylase, histone acetyl transferase, yeast Sin3 protein (which recruits Rpd3 (HDA complex) by binding to the DNA binding protein), Ume6, or transcriptional activators, for example but nit limited to VP16, Gal4, LexA; or
- a protein involved in protein-protein interaction, for example but not limited to chromatin remodelling proteins and HAT/HDA recruitment factors (Lusser A., Kolle D., Loidl P., 2001, Trends Plt. Sci. 6: 59-65); or
- a protein that does not directly interact with transcriptional processes but when bound to the operator sequence exhibits a property of blocking interaction of polymerase, or other factors required for transcription, with the promoter region, or migration of polymerase along a nucleic acid comprising the operator sequence, or both, blocks interaction of transcription factors with the promoter region and blocks polymerase migration.

Preferably the repressor protein or fusion protein comprises a nuclear localization signal so that the protein or fusion protein is directed to the nucleus.

By "codon optimization" it is meant the selection of appropriate DNA nucleotides for the synthesis of oligonucleotide building blocks, and their subsequent enzymatic assembly, of a structural gene or fragment thereof in order to approach codon usage within plants.

By "operator sequence" it is meant a sequence of DNA that can interact or bind with a DNA binding domain of a protein, for example, a repressor protein. An example of a repressor protein, or a DNA binding domain, that exhibits the property of binding to an operator sequence, and which is not to be considered limiting, is a ROS repressor, or the DNA binding domain of the ROS repressor, respectively. The operator sequence is preferably located in proximity of a gene of interest, either upstream of, downstream of, or within, the coding region of a gene, for example within an intron of a gene. When the repressor protein, or the DNA binding domain of the repressor, binds the operator sequence expression of the gene in operative association with the operator sequence is reduced. Preferably, the operator sequence is located in the proximity of a regulatory region that is in operative association with a gene of interest. However, the operator sequence may also be localized elsewhere within a first genetic construct to block migration of polymerase along the nucleic acid.

An operator sequence may consist of inverted repeat or palindromic sequences of a specified length. The ROS operator may comprise 9 or more nucleotide base pairs (see FIGS. 1(D) and (E)) that exhibits the property of binding a DNA binding domain of a ROS repressor. A consensus sequence of a 10 base pair region including the 9 base pair DNA binding site sequence is WATDHWKMAR (SEQ ID NO: 20; FIG. 1(E)). The last nucleotide, "R", of the consensus sequence is not required for ROS binding (data not presented). Examples of operator sequences, which are not to be considered limiting in any manner, also include, as is the case with the ROS operator sequence from the virC or virD gene promoters, a ROS operator made up of two 11 bp inverted repeats separated by TTTA:

TATATTTCAATTTTATTGTAATATA;      (SEQ ID NO:8)

the operator sequence of the IPT gene:

TATAATTAAAATATTAACTGTCGCATT.    (SEQ ID NO:19)

However, it is to be understood that analogs or variants of SEQ ID NO's:8, 19 and 20 may also be used providing they exhibit the property of binding a DNA binding domain, preferably a DNA binding domain of the ROS repressor. The ROS repressor has a DNA binding motif of the $C_2H_2$ zinc finger configuration. In the promoter of the divergent VirC/VirD genes of *Agrobacterium tumefaciens*, ROS binds to a 9 bp inverted repeat sequence in an orientation-independent manner (Chou et al., 1998, Proc. Natl. Acad. Sci., 95: 5293). The ROS operator sequence in the ipt promoter also consists of a similar sequence to that in the virC/virD except that it does not form an inverted repeat (Chou et al., 1998, Proc. Natl. Acad. Sci. USA, 95: 5293). Only the first 9 bp are homologous to ROS box in virC/virD indicating that the second 9 bp sequence may not be a requisite for ROS binding. Accordingly, the use of ROS operator sequences or variants thereof that retain the ability to interact with ROS, as operator sequences to selectively control the expression of genes or nucleoitide sequences of interest, is within the scope of the present invention.

By "regulatory region" or "regulatory element" it is meant a portion of nucleic acid typically, but not always, upstream of the protein coding region of a gene, which may be comprised of either DNA or RNA, or both DNA and RNA. When a regulatory region is active, and, in operative association with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well.

An inducible regulatory region is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory region to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, teracycline-inducible promoter (Gatz, C., 1997, Ann. Rev. Plant Physiol. Plant Mol. Biol.48, 89-108; which is incorporated by reference), steroid inducible promoter (Aoyama, T. and Chua, N. H., 1997, Plant J. 2,397-404; which is incorporated by reference) and ethanol-inducible promoter (Salter, M. G., et al, 1998, Plant Journal 16, 127-132; Caddick, M. X., et al,1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996, Plant J., 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

The regulatory regions of the first and second nucleotide sequences denoted above, may be the same or different. For example, which is not to be considered limiting in any manner, the regulatory elements of the first and second genetic constructs may both be constitutive. In this case, each of the first aid second nucleotide sequences are maintained in separate plants, a first and a second plant, respectively. The first nucleotide sequence encoding a gene of interest is expressed within the first plant. The second plant expresses the second nucleic acid sequence encoding a repressor protein. Crossing of the first and second plants produces a progeny that expresses the repressor protein but not the gene of interest. In this manner the expression of gene of interest that is required to maintain parent stocks may be retained within a parent plant but not expressed in a progeny plant. Such a cross may produce sterile offspring.

Alternatively, which is not to be considered limiting in any manner, either the second regulatory element may be active before, during, or after, the activity of the first regulatory element, thereby either initially repressing expression of the gene of interest followed by permitting the expression of the gene of interest or, following expression of the gene of interest, the second regulatory element becomes active which results in the repression of the expression of the gene of interest. Similarly, the first regulatory element maybe active before, during, or after, the activity of the second regulatory element. Other examples, which are not to be considered limiting, include the second regulatory element being an inducible regulatory element that is activated by an external stimulus so that repression of gene expression may be controlled through the addition of an inducer. The second regulatory element may also be active during a specific developmental stage preceding, during, or following that of the activity of the first regulatory element. In this way the expression of the gene of interest maybe repressed or activated as desired within a plant.

The present invention is therefore directed to one or more chimeric genetic constructs comprising a gene of interest operatively linked to a regulatory element where the regulatory element is in operative association with an operator sequence. Any exogenous gene can be used as a gene of interest and manipulated according to the present invention to result in the regulated expression of the exogenous gene. The present invention also pertains to one or more chimeric constructs comprising a regulatory element in operative association with a nucleic acid sequence encoding a repressor protein.

By "gene of interest", "nucleotide sequence of interest", or "coding region of interest" it is meant any gene, nucleotide sequence, or coding region that is to be expressed within a host organism. These terms are used interchangeably. Such a nucleotide sequence of interest may include, but is not limited to, a gene or coding region whose product has an effect on plant growth or yield, for example a plant growth regulator such as an auxin or cytokinin and their analogues, or a nucleotide sequence of interest may comprise a herbicide or a pesticide resistance gene, which are well known within the art. A gene or coding region of interest may encode an enzyme involved in the synthesis of, or in the regulation of the synthesis of, a product of interest, for example, but not limited to a protein, or an oil product. A nucleotide sequence of interest may encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

A nucleotide sequence, or coding region of interest may also include a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-$\alpha$, interferon-$\beta$, interferon-$\tau$, blood clotting factors, for example, Factor VIII, Factor IX, or tPA or combinations thereof. If the gene of interest encodes a product that is directly or indirectly toxic to the plant, then by using the method of the present invention, such toxicity may be reduced throughout the plant by selectively expressing the gene of interest within a desired tissue or at a desired stage of plant development.

A nucleotide sequence, or coding region of interest may also include a gene that encodes a protein involved in regulation of transcription, for example DNA-binding proteins that act as enhancers or basal transcription factors, histone deacetylases, or histone acetyl transferases. Moreover, a nucleotide sequence of interest may be comprised of a partial sequence or a chimeric sequence of any of the above genes, in a sense or antisense orientation.

It is also contemplated that a gene, or coding region of interest may be involved in the expression of a gene expression cascade, for example but not limited to a developmental cascade. In this embodiment, the gene of interest is preferably associated with a gene that is involved at an early stage within the gene cascade, for example homeotic genes. Expression of a gene of interest, for example a repressor of homeotic gene expression, represses the expression of a homeotic gene. Expression of the repressor protein within the same plant, either via crossing, inducuction, temporal or developmental expression of the regulatory region, as described herein, derepresses the expression of the homeotic gene thereby initiating a gene cascade. Homeotic genes are well known to one of skill in the art, and include but are hot limited to, transcription factor proteins and associated regulatory regions, for example controlling sequences that bind AP2 domain containing transcription factors, for example but not limited to, APETALA2 (a regulator of meristem identity, floral organ specification, seedcoat development and floral homeotic gene expression; Jofuku et al., 1994), CCAAT box-binding transcription factors (e.g. LEC1; WO 98/37184; Lotan, T., et al.,1998, Cell 93, 1195-1205), or the controlling factor associated with PICKLE, a gene that produces a thickened, primary root meristem (Ogas, J., et al,.1997, Science 277, 91-94).

A gene, or coding region of interest may also be involved in the control of transgenes across generations, or production of F1 hybrid plants with seed characteristics that would be undesirable in the parental line or progeny, for example but not limited to, oil seeds characterized as having reduced levels of sinapine biosynthesis within the oil-free meal. In this case, a gene of interest may be any enzyme involved in the synthesis of one or more intermediates in sinipine biosynthesis. An example, which is to be considered non-limiting, is caffeic o-methyltransferase (Acc# AAG51676), which is involved in ferulic acid biosynthesis. Other examples of genes of interest include genes that encode proteins involved in fiber, or glucosinolate, biosynthesis, or a protein involved in the biosynthesis of a phytotoxin. Phytotoxins may also be used for plant selection purposes. In this non-limiting example, a gene of interest may encode a protein that is capable of metabolizing a compound from a non-toxic form to a toxic form thereby selectively removing plants that express the gene of interest. The phytotoxic compound may be synthesized from endogenous precursors that are metabolized by the gene of interest into a toxic form, for example plant growth regulators, or the phytotoxic compound may be synthesized from an exogenously applied compound that is only metabolized into:a toxic compound in the presence of the gene of interest. For example, which is not to be considered limiting, the gene of interest may comprise indole acetamide hydrolase (IAH), that converts exogenously applied indole acetamide (IAM) or naphthaline acetemide (NAM), to indole acetic acid (IAA), or naphthaline acetic acid (NAA), respectively. Over-synthesis of IAA or NAA is toxic to a plant, however, in the absence of IAH, the applied IAM or NAM is non-toxic. Similarly, the gene of interest may encode a protein involved in herbicide resistance, for example, but not limited to, phosphinothricin acetyl transferase, wherein, in the absence of the gene-encoding the transferase, application of phosphinothricin, the toxic compound (herbicide) results in plant death. Other genes or coding regions of interest that encode lethal or conditionally lethal products may be found in WO 00/37660 (which is incorporated herein by reference).

The coding region of interest or the nucleotide sequence of interest may be expressed in suitable plant hosts which are transformed by the nucleotide sequences, or nucleic acid molecules, or genetic constructs, or vectors of the present invention. Examples of suitable hosts include, but are not limited to, agricultural crops including canola, *Brassica* spp., maize, tobacco, alfalfa, potato, ginseng, pea, oat, rice, soybean, wheat, barley, sunflower, and cotton. Any member of the *Brassica*-family can be transformed with one or more genetic constructs of the present invention including, but not limited to, canola, *Brassica napus, B. carinata, B. nigra, B. oleracea, B. chinensis, B. cretica, B. incana, B. insularis, B. japonica, B. atlantica, B. bourgeoaui, B. narinosa, B. juncea, B. rapa, Arabidopsis.*

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. One or more of the chimeric genetic constructs of the present invention can also include further enhancers, either translation or transcription enhancers, as maybe required. These enhancer regions are well known to persons skilled in the art, and can include the ATG initiation codon and adjacent sequences. The initiation codon must be in phase with the reading frame of the coding sequence to ensure translation of the entire sequence.

Examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene.

To aid in identification of transformed plant cells, the constructs of this invention may be further manipulated to include plant selectable markers. Useful selectable markers include enzymes which provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (β-glucuronidase), or luminescence, such as luciferase or GFP, are useful.

Also considered part of this invention are transgenic plants containing the chimeric gene construct of the present invention. However, it is to be understood that the chimeric gene constructs of the present invention may also be combined with gene of interest for expression within a range of plant hosts.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures (for example, Clough and Bent, 1998)

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, Methods for Plant Molecular Biology, Academy Press, New York VIII, pp. 421-463 (1988); Geierson and Corey, Plant Molecular Biology, 2d Ed. (1988); and Miki and Iyer, Fundamentals of Gene Transfer in Plants. In Plant Metabolism, 2d Ed. D T. Dennis, D H Turpin, D D Lefebrve, D B Layzell (eds), Addison Wesly, Langmans Ltd. London, pp. 561-579 (1997); Clough and Bent (1998)). The present invention further includes a suitable vector comprising the chimeric gene construct.

An "analogue" or "derivative" includes any substitution, deletion, or addition to the nucleotide or amino acid sequence of the repressor protein, for example but not limited to, the ROS repressor, provided that the analogue or derivative thereof, maintains the property of binding or associating with the operator sequence, ROS repressor activity, or both. Preferably, the repressor protein, or an analogue or derivative thereof exhibits the property of binding an operator sequence, and exhibits the property of repressing the expression of a gene in operative association with the operator sequence.

The DNA sequences of the present invention include the DNA sequences of SEQ ID NO: 1, 2 and 3 (native or wild-type ROS repressor, synthetic ROS repressor, and a composite or consensus ROS repressor; also see FIGS. 1(B) and-(C)) derivatives, and fragments thereof, as well as analogues of, or nucleic acid sequences that are substantially homologous to, and that exhibit greater than 80% similarity with, the nucleic acid sequence as defined in SEQ ID NO: 2 or 3. If a fragment of a ROS repressor is used, the fragment is at least of about 54 nucleotides in length in order to cover the zinc finger domain (from 249 to 303). Preferably, the fragment is from about 54 to about 150 nucleotides in length, more preferably from about 54 to about 80 nucleotides in length.

Sequences that exhibit greater than 80% similarity, may be determined by use of the BLAST algorithm originally described in Altschul et al., J. Mol. Biol. 215(3): 403-10, 1990, updated versions available from NCBI), using default parameters (Program: blastn; Database: nr; Expect 10; filter: low complexity; Alignment: pairwise; Word size: 11). Analogs, or derivatives thereof, also include those DNA sequences which hybridize under stringent hybridization conditions (see Maniatis et al., in Molecular Cloning (A Laboratory Manual), Cold Spring Harbor Laboratory, 1982, p. 387-389) to any one of the DNA sequences of SEQ ID NO: 1, 2 or 3 provided that the sequences exhibit the property of binding an operator sequence (operator binding activity), or maintain the property of repressing the expression of a gene in operative association with the operator sequence. An example of one such stringent hybridization conditions may be hybridization with a suitable probe, for example but not limited to, a [$\alpha$-$^{32}$P]dATP labelled probe for 16-20 hrs at 65° C. in 7% SDS, 1mM EDTA, 0.5M $Na_2HPO_4$, pH 7.2. Followed by washing in 5% SDS, 1mM EDTA 40mM $Na_2HPO_4$, pH 7.2 for 30 mm followed by washing in 1% SDS, 1mM EDTA 40mM $Na_2HPO_4$, pH 7.2 for 30 min. Washing in this buffer may be repeated to reduce background. An example of an analog or a derivative of the ROS repressor, which is not to be considered limiting in any manner, includes the ROS operator binding sequence fused to a second protein to produce a fusion protein, providing that the fusion protein exhibits ROS operator sequence binding activity.

The second protein that is fused to the DNA binding sequence, may be any protein, including a protein having an activity that regulates gene expression when bound to the operator sequence, for example but not limited to histone deacetylase, histone acetyl transferase, a protein involved in protein-protein interaction, or a protein that does not directly interact with transcriptional processes, but that exhibits a characteristic of steric hindrance, for example, interfering with the association of polymerase or other transcription factor within the promoter region, or by blocking migration of polymerase along a nucleic acid.

Figure 3A:
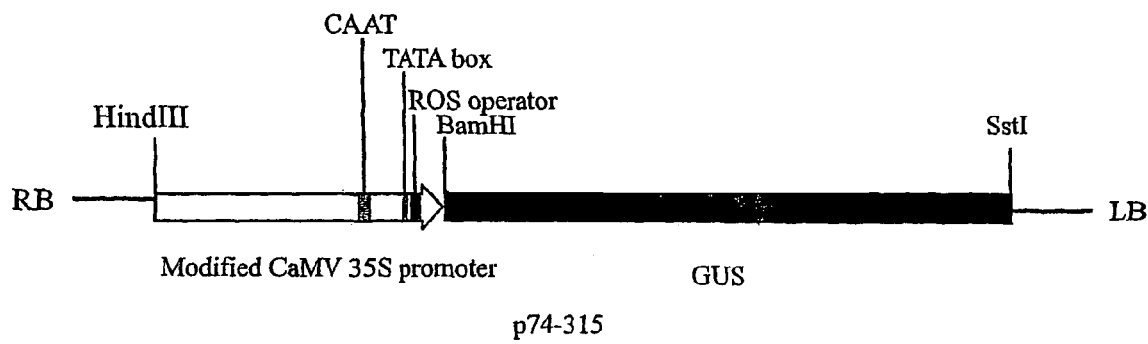
FIG. 3(A) shows the nucleotide construct p74-315 in which a CaMV35S regulatory region, modified to contain a ROS operator site downstream of the TATA box, is operatively linked to a gene of interest (β-glucuronidase; GUS).
Figure 3B:
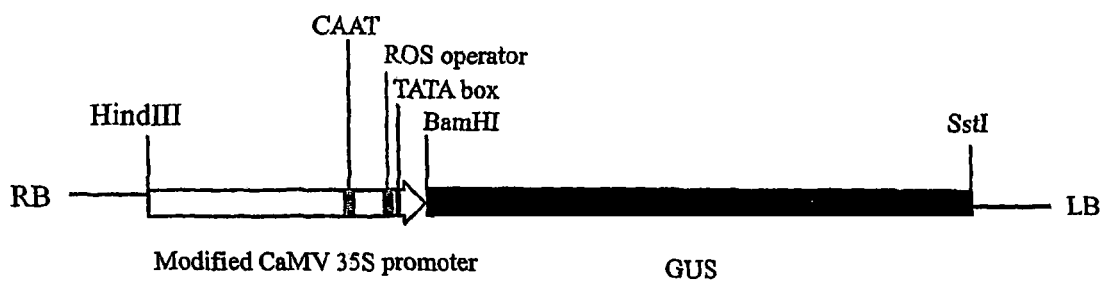
FIG. 3(B) shows the nucleotide construct p74-316 in which a CaMV35S regulatory region is modified to contain a ROS operator site upstream of the TATA box is operatively linked to the protein encoding region of GUS.
Figure 3C:
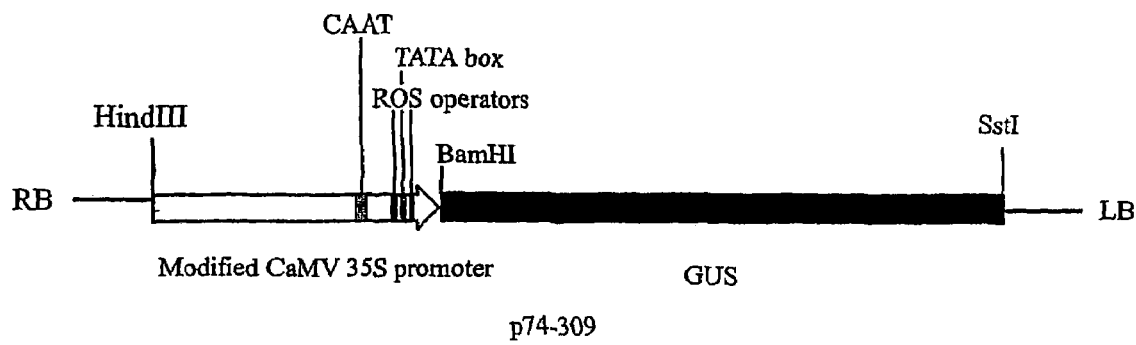
FIG. 3(C) shows the nucleotide construct p74-309 in which a CaMV35S regulatory region modified to contain ROS operator sites upstream and downstream of the TATA box is transcriptionally fused (i.e. operatively linked) to the protein encoding region of GUS.
Figure 4A:
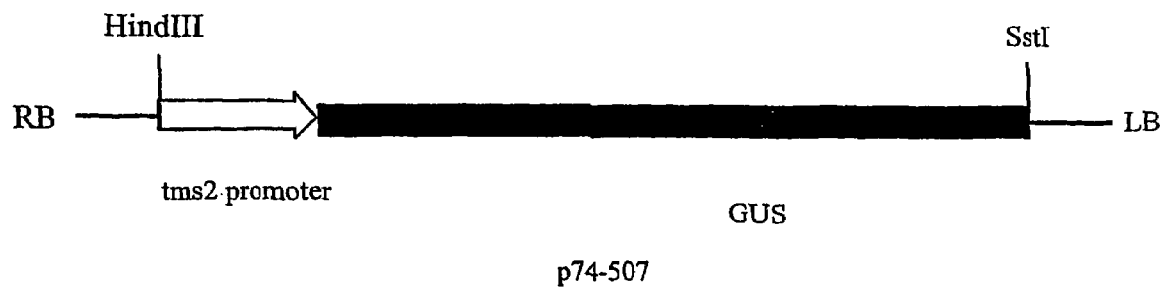
FIG. 4(A) shows the nucleotide construct p76-507 in which a tms2 regulatory region is operatively linked to a gene of interest (in this case encoding β-glucuronidase, GUS).
Figure 4B:
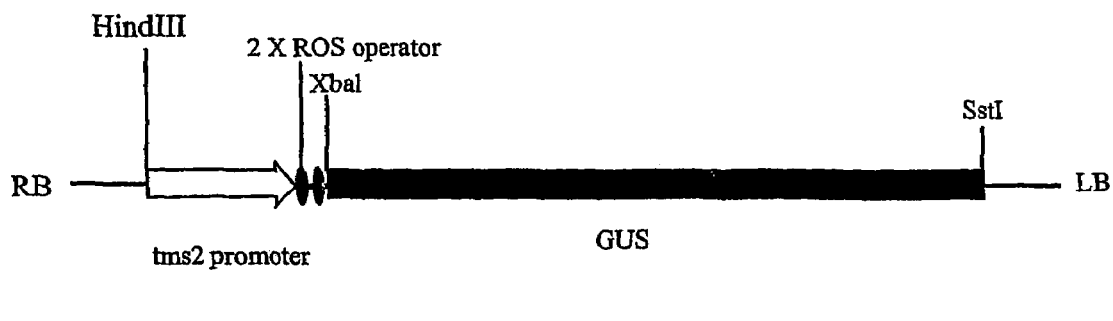
FIG. 4(B) shows the nucleotide construct p76-508 in which a tms2 regulatory region modified to contain two tandemly repeated ROS operator sites downstream of the TATA box is transcriptionally fused (i.e. operatively linked) to the protein coding region of GUS.
Figure 5A:
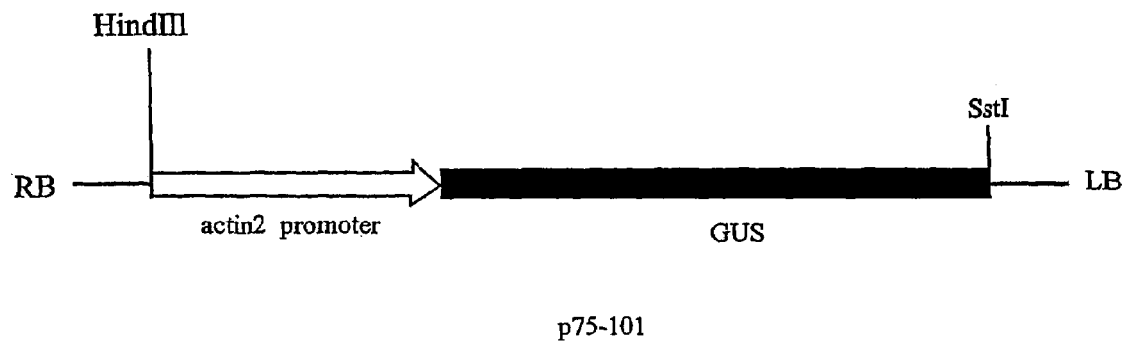
FIG. 5(A) shows the nucleotide construct p75-101 in which an actin2 regulatory region is operatively linked to a gene of interest (the β-glucuronidase (GUS) reporter gene).
Figure 5B:
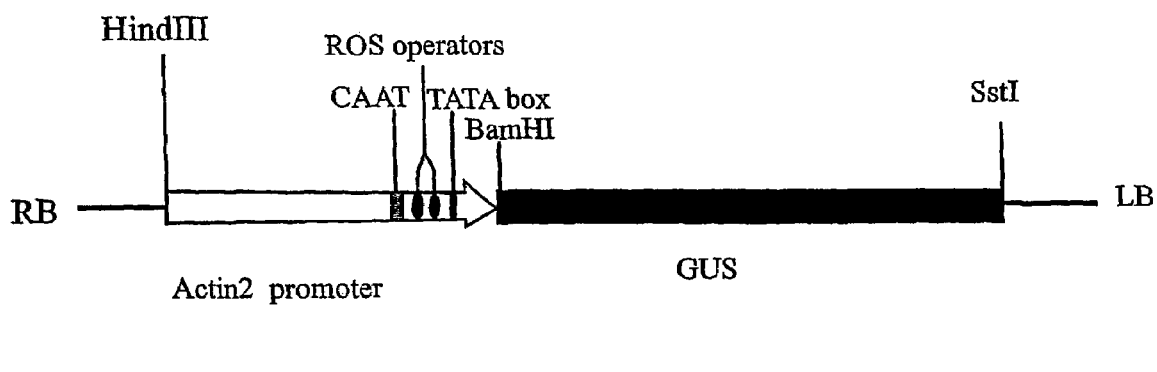
FIG. 5(B) shows the nucleotide construct p74-501 in which an actin2 regulatory region modified to contain two tandemly repeated ROS operator sites upstream of the TATA box is transcriptionally fused (operatively linked) to the a gene of interest (GUS).

The present invention is further directed to one or more nucleotide constructs comprising a nucleotide sequence (coding region) of interest operatively linked to a regulatory region that is modified to contain one or more operator sequences, for example, but not limited to, one or more ROS operator sequences (see FIGS. 3, 4, or 5). As shown in FIG. 3 an operator sequence may be placed downstream (FIG. 3(A)), upstream (FIG. 3(B)), or upstream and downstream (FIG. 3(C)) of the TATA box within a regulatory region. The operator sequences may be placed within a promoter region as single binding elements or as tandem repeats (see FIG. 5(B)). Furthermore, as shown in FIG. 4(B)), tandem repeats of an operator sequence can be placed downstream of the entire promoter or regulatory region and upstream of the gene or nucleotide sequence of interest. An operator sequence, or repeats of an operator sequence may also be positioned within untranslated or translated leader sequences (if positioned in-frame), introns of a gene, or within an ORF of a gene, if inserted in-frame. Any gene or nucleotide sequence may be used as the gene or nucleotide sequence of interest and be selectively targeted for regulation of gene expression according to the present invention.

The repressor protein that is produced from the second nucleotide sequence, for example but not limited to a ROS repressor, can bind to operator sequences contained within the regulatory region of the first nucleotide sequence and thereby specifically and selectively repress transcription of the gene of interest. Preferably, the first nucleotide sequence and the second nucleotide sequence are chromosomally integrated into a plant or plant cell. The two nucleotide sequences may be integrated into two different genetic loci of a plant or plant cell, or the two nucleotide sequences may be integrated into a singular genetic locus of a plant or plant cell.

The ROS transcription factor (ROS repressor, FIG. 1(A); SEQ ID NO:3), for example, of *Agrobacterium tumefaciens* (SEQ ID NO's:1 and 21, nucleic acid and amino acid sequence, respectively) has a DNA binding motif (see bolded amino acids, FIG. 1(C)) of the $C_2H_2$ zinc finger configuration (Chou et al., 1998, Proc. Natl. Acad. Sci., 95: 5293). Zinc finger DNA binding proteins represent a significant portion of transcription factors in eukaryotes, but are rare in prokaryotes. The zinc finger ROS protein varies from its counterparts in eukaryotes in two aspects:

1. Unlike most eukaryotic zinc finger proteins, which contain multiple zinc finger motifs, the ROS repressor has only one such motif.
2. There are 9 amino acid residues making up the peptide loop spacing the zinc finger motif in the ROS repressor as compared to the 12 amino acids that make up the loops of zinc fingers of eukaryotic proteins.

These two characteristics of the ROS zinc finger motif, and possibly, the small size of the ROS repressor (~15.5 kDa) provide structural uniqueness and molecular flexibility and that make the ROS repressor, or analogs thereof, a suitable candidate as a transcription factor for regulation of gene expression in plants. However, it is to be understood that larger size chimeric proteins comprising a ROS operator binding domain may also be used as described herein.

The ROS repressor is encoded by a nucleotide sequence of bacterial origin and, as such the nucleotide sequence may be optimised, for example, by changing its codons to favour plant codon usage (e.g. SEQ ID) NO:2), by attaching a nucleotide sequence encoding a nuclear localisation signal, for example but not limited to SV40 localization signal (see Robbins et al., 1991, Cell, 64: 615-623; Rizzo, P., Di Resta, I., Powers, A., Ratner, H. and Carbone, M. 1991, Cancer Res. 59 (24), 6103-6108; which are incorporated herein by reference) in order to improve the efficiency of ROS transport to the plant nucleus to facilitate the interaction with its respective operator, or both optimizing plant codon usage and fusing a nuclear localization signal to the ROS repressor nucleic acid sequence. Other possible nuclear localization signals that may be used include but are not limited to those listed in Table 1:

TABLE 1 nuclear localization signals

| Nuclear Protein | Organism | NLS | Ref |
| --- | --- | --- | --- |
| AGAMOUS | A | RienttnrqvtfcKRR | 1 (SEQ ID NO: 31) |
| TGA-1A | T | RRlaqnreaaRKsRlRKK | 2 (SEQ ID NO: 32) |
| TGA-1B | T | KKRaRlvrnresaqlsRqRKK | 2 (SEQ ID NO: 33) |
| O2 NLS B | M | RKRKesnresaRRsRyRK | 3 (SEQ ID NO: 34) |
| NIa | V | KKnqkhklkm-32aa-KRK | 4 (SEQ ID NO: 35) |
| Nucleoplasmin | X | KRpaatkkagqaKKKKl | 5 (SEQ ID NO: 36) |
| NO38 | X | KRiapdsaskvpRKKtR | 5 (SEQ ID NO: 37) |
| N1/N2 | X | KRKteeesplKdKdaKK | 5 (SEQ ID NO: 38) |
| Glucocorticoid |  |  |  |
| receptor | M, R | RKclqagmnleaRKtKK | 5 (SEQ ID NO: 39) |
| α receptor | H | RKclqagmnleaRKtKK | 5 (SEQ ID NO: 40) |
| β receptor | H | RKclqagmnleaRKtKK | 5 (SEQ ID NO: 41) |
| Progesterone receptor | C, H, Ra | RKccqagmvlggRKfKK | 5 (SEQ ID NO: 42) |
| Androgen receptor | H | RKcyeagmtlgaRKlKK | 5 (SEQ ID NO: 43) |
| p53 | C | RRcfevrvcacpgRdRK | 5 (SEQ ID NO: 44) |

[+]A, *Arabidopsis*; X, *Xenopus*; M, mouse; R, rat; Ra, rabbit; H, human; C, chicken; T, tobacco; M, maize; V, potyvirus.
References:
1, Yanovsky et al., 1990, Nature, 346: 35-39
2, van der Krol and Chua, 1991, Plant Cell, 3: 667-675
3, Varagona et al., 1992, Plant Cell, 4: 1213-1227
4, Carrington et al., 1991, Plant Cell, 3: 953-962
5, Robbins et al., 1991, Cell, 64: 615-623

The fusion of a nuclear localization signal to the repressor protein or fusion protein facilitates migration of the repressor, or fusion, protein into the nucleus. Without wishing to be bound by theory, reduced levels of repressor or fusion proteins elsewhere within the cell may be important when the repressor or fusion protein may bind analogue operator sequences within other organelles, for example within the mitochondrion or chloroplast. Furthermore, the use of a nuclear localization signal may permit the use of a less active promoter or regulatory region to drive the expression of the repressor, or fusion, protein while ensuring that the concentration of the expressed protein remains at a desired level within the nucleus, and that the concentration of the protein is reduced elsewhere in the cell.

The nuclear localization signal may be fused to the N, C, or both the N and C terminus of the ROS protein. Furthermore, the nuclear localization signal may be fused within the coding region of the gene, provided that the activity of the protien is retained. Preferably, the nuclear localization signal is fused to the carboxy-terminus of the protein or fusion protien. The nucleotide sequence, depicted in FIG. 1(B) or SEQ ID NO:2, consisting of the fusion of the modified nucleotide sequence of the protein coding region of ROS with the nucleotide sequence encoding the nuclear localization signal is designated as "synthetic ROS". Thus, analogues of the nucleotide sequence encoding ROS repressor, or the amino acid sequence of the ROS repressor, are within the scope of the present invention.

In order to optimize expression levels and transgene protein production of a repressor protein, for example the ROS repressor, the nucleic acid sequence of the ROS repressor was examined and the coding region modified to optimize for expression of the gene in plants. A procedure similar to that outlined by Sardana et al. (Plant Cell Reports 15:677-681; 1996) may also be used. A table of codon usage from highly expressed genes of dicotyledonous plants was compiled using the data of Murray et al. (Nuc Acids Res. 17:477-498; 1989). An example of a synthetic ROS repressor gene comprising codons optimized for expression within plants is shown in FIG. 1(B). However, it is to be understood that other base pair combinations may be used for the preparation of a synthetic ROS repressor gene, for example SEQ ID NO:3, using the methods as described herein in order to optimize ROS repressor expression within a plant.

Assembly of the synthetic ROS repressor gene of this invention is performed using standard technology know in the art. The gene may be assembled enzymatically, within a DNA vector, for example, using PCR, or synthesised from chemically synthesized oligonucleotide duplex segments. The synthetic gene is then introduced into a plant using methods known in the art. Expression of the gene maybe determined using methods known within the art, for example Northern analysis, Western analysis, or ELISA.

The present invention also pertains to the regulation of gene expression in plants using the ROS repressor protein, whereby the ROS repressor is used as a regulatory switch to repress the expression of selected coding regions or nucleotide sequences of interest. The repression of the expression of a gene of interest may be accomplished by transforming the plant with two constructs:

1. A first genetic construct comprising a gene or nucleotide sequence of interest operatively associated with a regulatory region containing at least one operator sequence that can interact with the ROS repressor.

2. A second genetic construct comprising an appropriate regulatory region operatively linked to a nucleotide sequence that encodes the ROS repressor.

The first and second genetic constructs may be inserted into a plant in separate vectors, each of which maybe introduced into a plant via co-transformation sequentially, or at the same time, or introduced into a plant by crossing plants expressing either the first or second genetic construct, or both genetic constructs may reside within one vector, and be introduced within a plant at the same time.

Preferably, the protein coding region of the nucleotide sequence encoding the ROS repressor is modified to favour plant codon usage. Furthermore, it is preferred that the nucleotide sequence is operatively linked with a nucleotide sequence encoding a nuclear localisation signal. Expression of both constructs within the same plant will result in a repression of the expression of the gene of interest as mediated by an interaction of the ROS repressor with a ROS operator sequence contained within the regulatory region of the first genetic construct.

Figure 2A:
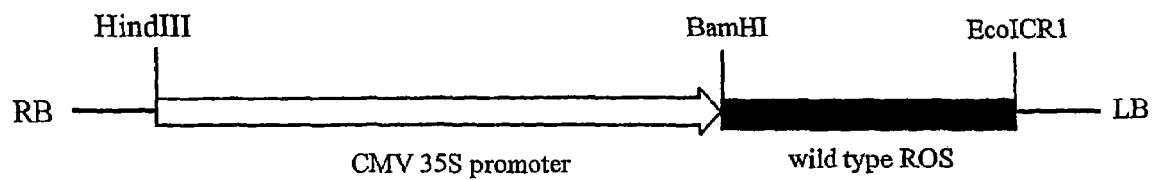
FIG. 2(A) shows a schematic diagram of the p74-107 nucleotide construct in which a CaMV35S regulatory region is operatively linked to the wild type ROS protein coding region.
Figure 2B:
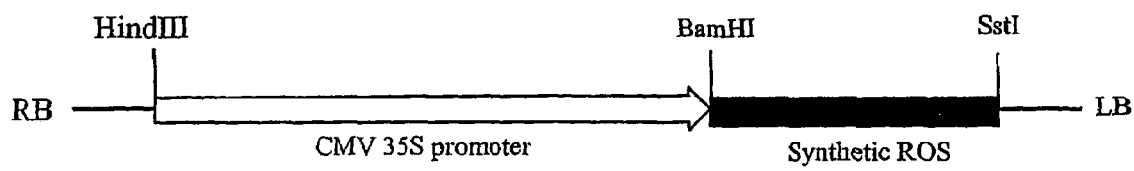
FIG. 2(B) shows the nucleotide construct p74-313 in which a CaMV35S regulatory region is operatively linked (transcriptionally fused) to the protein coding region of synthetic ROS.
Figure 2C:
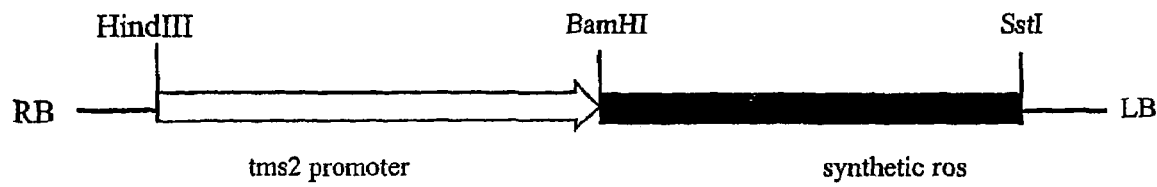
FIG. 2(C) shows the nucleotide construct p74-108 in which a trns2 regulatory region is transcriptionally fused to the protein coding region of synthetic ROS.

Schematic representations of constructs capable of expressing synthetic ROS or wild type ROS are shown in FIG. 2(A; wild type ROS) and FIGS. 2(B)-(D; synthetic ROS). Southern analysis (FIG. 6(B)) of *Arabidopsis* plants that are transformed with constructs comprising the second nucleic acid sequence of the present invention, expressing ROS repressor protein, indicates that both the wild type ROS and the synthetic ROS are integrated into the chromosome of *Arabidopsis*. Western blots shown in FIG. 7 demonstrate that both native ROS and synthetic ROS may be expressed within plants.

Figure 6A:
FIG. 6(A) shows Southern analysis of a plant comprising a first genetic construct, p74-309 (35S-operator sequence-GUS; see FIG. 3(C) for map).
Figure 8:
FIG. 8 shows expression of a gene of interest in plants. Upper panel shows expression of GUS under the control of 35S (pBI121; 35S:GUS). Middle panel shows GUS expression under the control of actin2 coprising ROS operator sequences (p74-501; see FIG. 5(B) for construct). Lower panel shows the lack of GUS activity in a non-transformed control.
Figure 8:

Similarly, stable integration and expression of the first nucleotide sequence of the present invention comprising a gene of interest, in operative association with a regulatory region which is in operative association with an operator sequence is seen in FIG. 6(A) (Southern analysis) and FIG. 8 (GUS expression).

Crossing plants expressing the first nucleotide sequence, comprising a gene or coding region of interest, for example but not limited to GUS, and the second nucleotide sequence encoding ROS repressor, either native or synthetic ROS, exhibit reduced expression of the coding region of interest, in this case GUS. Results of a cross between a transgenic line expressing synthetic ROS (ROS parent) and a nucleotide sequence of interest, for example, but not limited to GUS (GUS parent), are presented in FIG. 9 and demonstrate ROS mediated repression of a gene of interest.

As shown in FIG. 9A, GUS activity is detected in the GUS parent (expressing p74-118; see FIG. 5C for construct) but not in the ROS parent (p74-101; see FIG. 2D for construct), or in the progeny of the cross between the ROS and GUS parents (cross between plant lines expressing p74-101 and p74-118). The parent plants each expressed either GUS or ROS RNA as expected (FIG. 9B), yet no GUS RNA was detected in the progeny arising from a cross between the ROS and GUS parents. Southern analysis of the progeny of the cross between the GUS and ROS parents indicates that the progeny plant from the cross between the ROS and GUS parent comprised genes encoding both GUS and ROS (FIG. 9C).

Figure 10A:
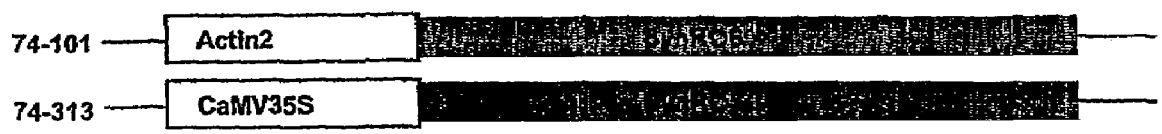
FIG. 10A shows two non-limiting examples of a second nucleotide sequence (repressor construct), p74-101 (Actin2 promotersynRos) and p74-313 (35S promoter-synRos).
Figure 10B:
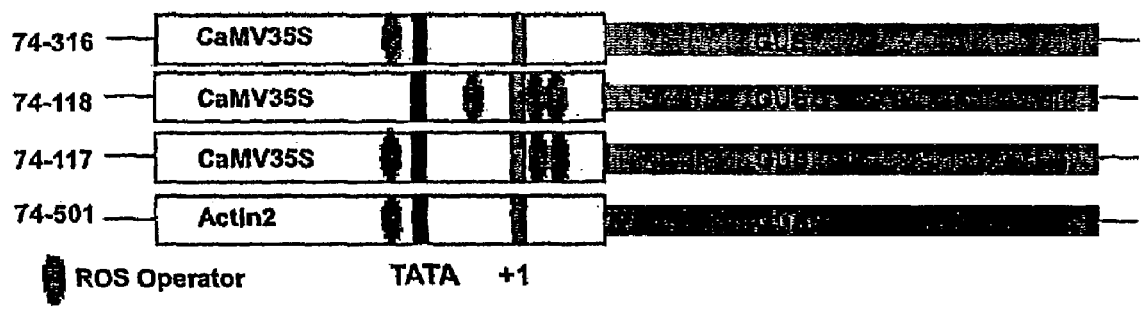
FIG. 10B shows several non-limiting examples of a first nucleotide sequence ((reporter constructs) including p74-316 (35S-1xOS-GUS; the OS is placed prior to the TATA sequence), p74-118 (35S-3xOS-GUS; all OS's after TATA sequence), p74-117 (35S-3xOS-GUS; one OS placed prior to TATA sequence), p74-501 (Actin 2-1xOS-GUS; OS placed prior to TATA sequence). The operator sequence (OS) is shown as a filled oval.
Figure 11B:
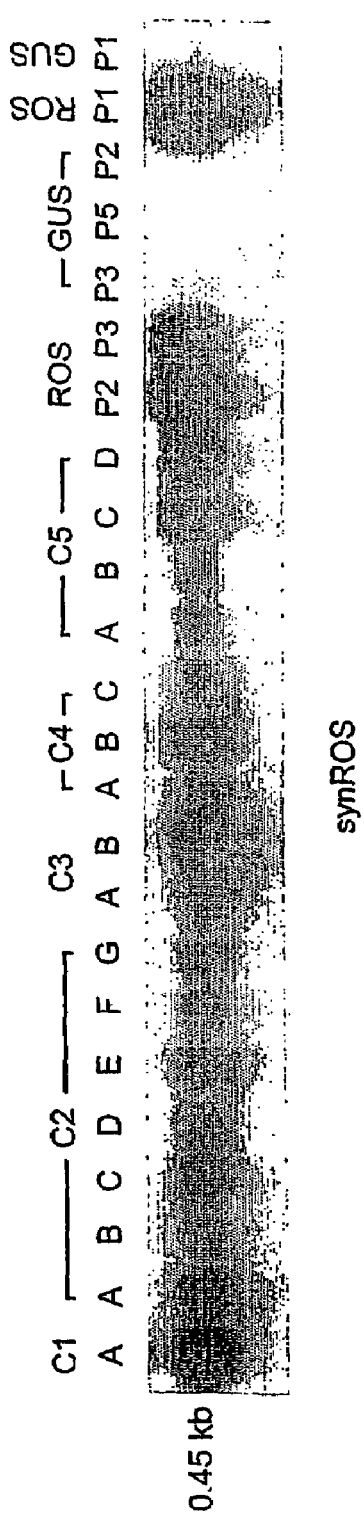
Figure 11C:
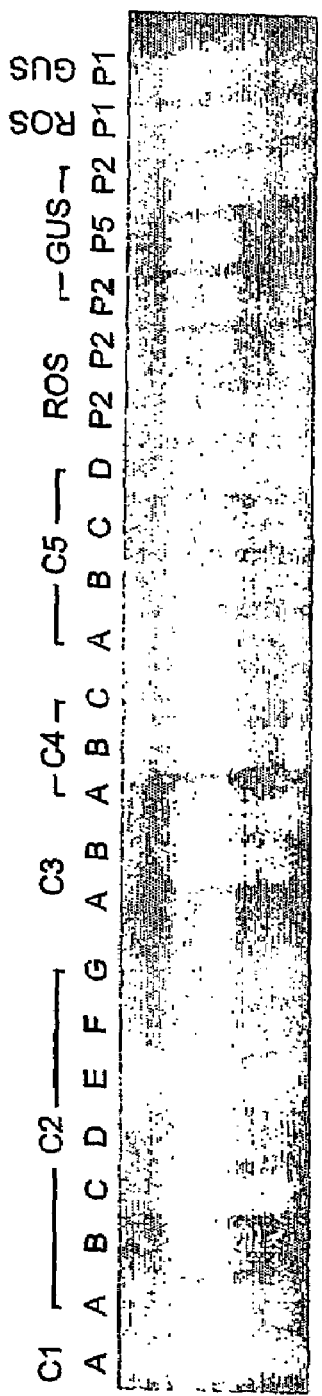
Figure 11D:
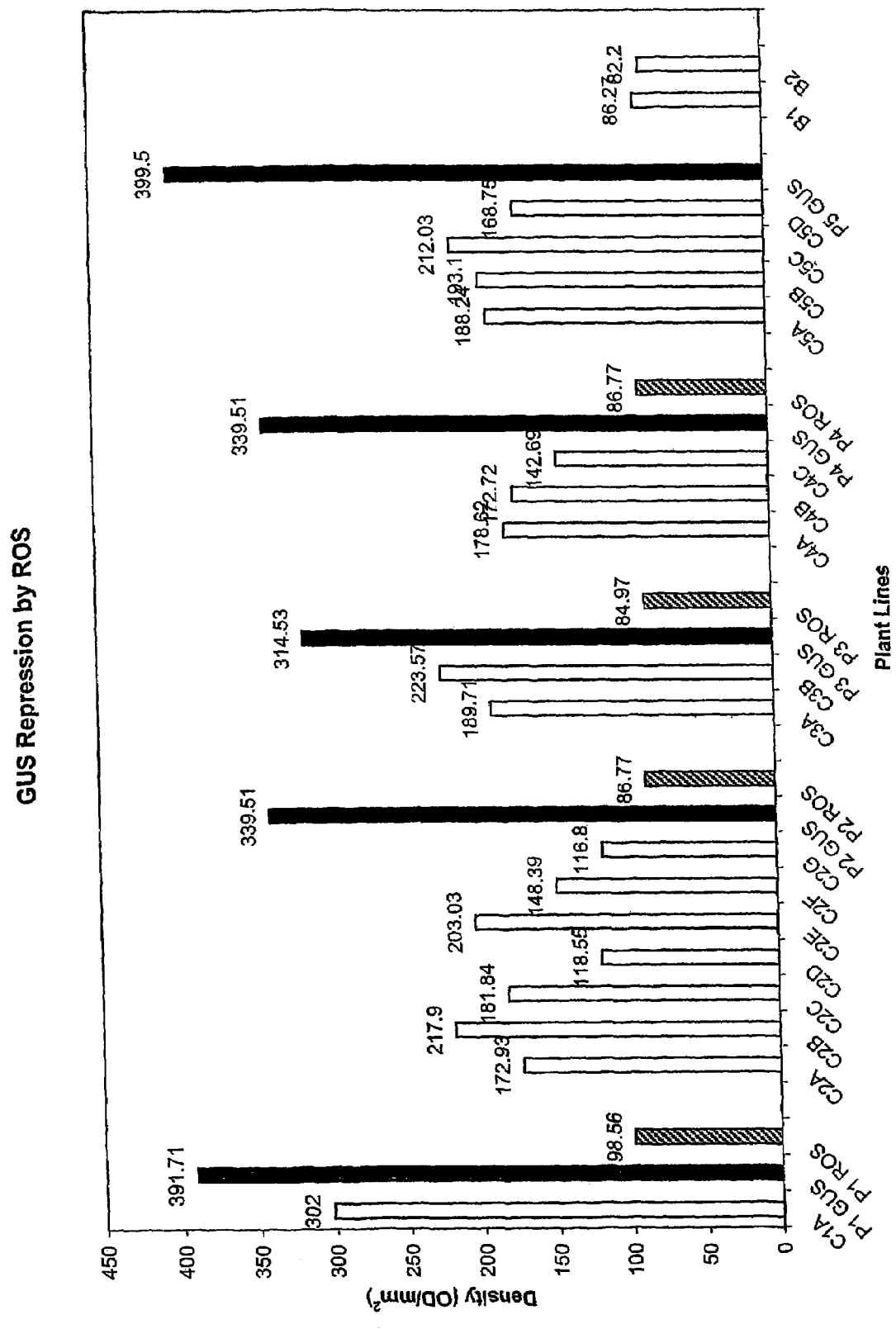
FIG. 11 shows Northern analysis and GUS activity of several parental lines, and progeny from crosses of parental lines expressing a first and a second nucleotide sequence.

Similar results of the inhibition of expression of a coding region of interest from about 20 to about 95% inhibition (of the expression observed in the parental lines), is also observed in a variety of crosses made between platform plants expressing a first nucleotide sequence comprising a regulatory region with one, or more than one operator sequences operatively linked with a coding region of interest (e.g. reporter construct; see FIG. 10B for non-limiting examples of constructs) and plants expressing a repressor (see FIG. 10A for non-limiting examples of constructs) as shown in FIG. 11A (GUS expression) and FIG. 11B (ROS expression; see Table 5 of the Examples, or the figure legend to FIG. 11, for a description of the crosses), FIG. 11D shows quantification of the data of FIG. 11A (using a GUS probe). As an example, progeny of a cross, C2, between a plant line comprising a first nucleotide sequence, p74-316 (35S-1x OS-GUS), and a plant line comprising a second nucleotide sequence, p74-101 (Actin2-syn-Ros) resulted in reduced expression of GUS (FIG. 11A, lanes C2 A-G) compared to GUS expression in the parent plants, P2 GUS or P2 ROS. Quantification of GUS RNA for this cross is provided in FIG. 11D (lanes C2A-G, and P2 GUS.

FIG. 13 provides further evidence for inhibition of expression of a coding region of interest by a repressor protein (as compared to expression of the coding region of interest in a parental cell line that does not produce a repressor) where the coding region of interest is operatively linked to a regulatory region that is able to be controlled by one, or more than one operator sequences that can bind or interact with the repressor. FIG. 12A shows the structure of a repressor construct (a non-limiting example of a second genetic construct of the invention) in which an actin2 regulatory region is operatively linked to a protein coding region of synthetic ROS. FIG. 12B shows the structure of a construct encoding a GUS reporter (a non-limiting example of a first genetic construct of-the invention) in which a CaMV35S regulatory region, modified to contain 4 ROS operator sequences, is operatively linked to a coding region of interest encoding GUS. Parental lines separately comprising a first nucleotide sequence comprising a coding region of interest (for example, a GUS reporter) and a second nucleotide sequence comprising a region coding for a repressor (for example, a ROS repressor) are crossed to produce plants comprising both first and second nucleotide sequences and the expression of the coding region of interest can be analyzed by any standard method. As shown in FIG. 13B levels of expression of a GUS reporter gene in crosses and parental lines is analyzed by Northern blot with densitometry analysis of the Northern blot shown in FIG. 13C.

These data further demonstrates that progeny of a cross between a plant expressing a first nucleotide sequence (comprising a coding region of interest) and a plant expressing a second nucleotide sequence (comprising a repressor) exhibit reduced levels of expression, of from about 20% to about 95%, of a coding region of interest.

These data demonstrate that expression of a gene of interest can be controlled using the repressor mediated system as described herein.

Examples of suitable hosts include, but are not limited to, agricultural crops including canola, *Brassica* spp., maize, tobacco, alfalfa, potato, ginseng, pea, oat, rice, soybean, wheat, barley, sunflower, and cotton. Any member of the *Brassica*-family can be transformed with one or more genetic constructs of the present invention including, but not limited to, *Arabidopsis, Brassica amplexicaulis, Brassica atlantica, Brassica balearica, Brassica barrelieri, Brassica bourgeaui, Brassica carinata* (Abyssinian mustard), *Brassica chinensis, Brassica cretica, Brassica deflexa, Brassica erucastrum, Brassica hilarionis, Brassica incana, Brassica insularis, Brassica insularis* subsp. *insularis, Brassica juncea* (Indian mustard), *Brassica macrocarpa, Brassica maurorum, Brassica montana, Brassica napus* (rape), *Brassica napus* var. *napobrassica* (Swedish turnip), *Brassica napus* var. *napus* (canola), *Brassica narinosa, Brassica nigra* (black mustard), *Brassica oleracea, Brassica oleracea* var. *acephala* (kale), *Brassica oleracea* var. *alboglabra* (Chinese kale), *Brassica oleracea* var. *botrytis* (cauliflower), *Brassica oleracea* var. *capitata* (cabbage), *Brassica oleracea* var. *gemmifera* (brussel sprouts), *Brassica oleracea* var. *gongylodes* (kohlrabi), *Brassica oleracea* var. *italica* (asparagus broccoli), *Brassica oleracea* var. *medullosa* (marrow-stem kale), *Brassica oleracea* var. *oleracea, Brassica oleracea* var. *ramosa* (branching bush kale), *Brassica oxyrrhina, Brassica rapa* (field mustard), *Brassica rapa* subsp. *chinensis* (bok-choy), *Brassica rapa* subsp. *oleifera* (biennial turnip rape), *Brassica rapa* subsp. *pekinensis* (Chinese cabbage), *Brassica rapa* subsp. *rapa* (turnip), *Brassica rupestris, Brassica tournefortii, Brassica villosa*.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Materials and Methods

Plant Material

Wild type *Arabidopsis thaliana*, ecotype Columbia, seeds were germinated on Redith (W.R. Grace & Co., Ajax, On) soil in pots covered with window screens under green house conditions (~25° C., 16 hr light). Emerging bolts were cut back to encourage further bolting. Plants were used for transformation once multiple secondary bolts had been generated.

Plant Transformation

Plant transformation was carried out according to the floral dip procedure described in Clough and Bent (1998, Plant J., 16, 735). Essentially, *Agrobacterium tumefaciens* transformed with the construct of interest (using standard methods as known in the art) was grown overnight in a 100 ml Luria-Bertani Broth (10 g/L NaCl, 10 g/L tryptone, 5 g/L yeast extract) containing 50 ug/ml kanamycin. The cell suspension culture was centrifuged at 3000×g for 15 min. The pellet was resuspended in 1 L of the transformation buffer (sucrose (5%), Silwet L77 (0.05%)(Loveland Industries, Greeley, Colo.)). The above-ground parts of the *Arabidopsis* plants were dipped into the *Agrobacterium* suspension for ~1 min and the plants were then transferred to the greenhouse. The entire transformation process was repeated twice more at two day intervals. Plants were grown to maturity and seeds collected. To select for transformants, seeds were surface sterilized by washing in 0.05% Tween 20 for 5 minutes, with 95% ethanol for 5 min, and then with a solution containing sodium hypochlorite (1.575%) and Tween 20 (0.05%) for 10 min followed by 5 washings in sterile water. Sterile seeds were plated onto either Pete Lite medium (20-20-20 Peter's Professional Pete Lite fertilizer (Scott, Marysville, Ohio) (0.762 g/l), agar (0.7%), kanamycin (50 ug/ml), pH 5.5) or MS medium (MS salts (0.5×)(Sigma), B5 vitamins (1×), agar (0.7%), kanamycin (50 ug/ml) pH 5.7). Plates were incubated at 20° C., 16 hr light/8 hr dark in a growth room. After approximately two weeks, seedlings possessing green primary leaves were transferred to soil for further screening and analysis.

Example 1

Optimization of ROS Protein Coding Region

The ros nucleotide sequence is derived from *Agrobacterium tumefaciens* (SEQ ID NO:1; FIG. 1A). Analysis of the protein coding region of the ros nucleotide sequence indicates that the codon usage may be altered to better conform to plant translational machinery. The protein coding region of the ros nucleotide sequence was therefore modified to optimize expression in plants (SEQ ID NO:2; FIG. 1B). The nucleic acid sequence of the ROS repressor was examined and the coding region modified to optimize for expression of the gene in plants, using a procedure similar to that outlined by Sardana et al. (Plant Cell Reports 15:677-681; 1996). A table of codon usage from highly expressed genes of dicotyledonous plants was compiled using the data of Murray et al. Nuc Acids Res. 17:477-498; 1989). The ros nucleotide sequence was also modified (SEQ ID NO:2; FIG. 1B) to ensure localization of the ROS repressor to the nucleus of plant cells, by adding a SV40 nuclear localization signal (Rizzo, P., Di Resta, I., Powers, A., Ratner, H. and Carbone, M. Cancer Res. 59 (24), 6103-6108 (1999; The nuclear localization signal resides at amino acid positions 126-132; accession number AAF28270).

The ros gene is cloned from *Agrobacterium tumefaciens* by PCR. The nucleotide sequence encoding the ROS protein is expressed in, and purified from, *E. coli*, and the ROS protein used to generate an anti-ROS antiserum in rabbits using standard methods (Maniatis et al.).

Example 2

Constructs that Express Synthetic ROS Repressor, or Wild Type ROS Repressor and Preparation of Repressor Lines The protein coding region of the ros gene is modified to favour *Arabidopsis thaliana* and *Brassica napus* codon usage, and in some constructs, to incorporate a nucleotide sequence encoding a nuclear localization signal at its carboxy terminus as described below. A modified ros nucleotide sequence comprising optimized codons and the nuclear localization signal is referred to as "synthetic ROS". In this example, the ROS coding portion of the synthetic ROS nucleotide sequence is designed to encode the same protein as the wild type bacterial ros nucleotide sequence, while optimizing codon usage in plants or plant cells.

p74-107: Construct for The Expression of The Wild Type ROS Driven by The CaMV 35S Promoter (FIG. 2(A)).

The protein coding region of the wild type ROS gene is amplified by PCR using total genomic DNA of *Agrobacterium tumefaciens* 33970 and the following two primers with built-in BamHI (G GAT CC) and HindIII (A AGC TT) sites:

```
Sense primer:
                                          (SEQ ID NO:4)
5-GCG GAT CCG ATG ACG GAA ACT GCA TAC-3'

Anti-sense primer:
                                          (SEQ ID NO:5)
5'-GCA AGC TTC AAC GGT TCG CCT TGC G-3'.
```

The PCR product, which lacks any nuclear localization signal, is cloned into the BamHI/HindIII sites of the pGEX vector (Pharmacia), excised from pGEX as a XhoI/BamHI fragment, and the Xho I site blunt-ended using Klenow. The resulting fragment is cloned into the BamHI/EcoICR1 sites of pBI121 (Clontech, Palo Alto, Calif.).

p74-313: Construct for The Expression of The Synthetic ROS Driven by The CaMV 35S Promoter (FIG. 2(B)).

The ORF of the ROS repressor is re-synthesized to favor plant codon usage as outlined above, and to incorporate a SV40 nuclear localization signal, PKKKRKV, at its carboxy terminus. The re-synthesized ROS is cloned into the BamHI-SacI sites of pUC19, and subcloned into pBI121 as a BamHI/SstI fragment replacing the GUS ORF in this vector.

p74-108: Construct for The Expression of The Synthetic ROS Repressor Driven by the tms2 Promoter (FIG. 2(C)).

The tms2 promoter is PCR amplified from genomic DNA of *Agrobacterium tumefaciens* 33970 using the following two primers:

```
sense primer:
5'-TGC GGA TGC ATA AGC TTG CTG ACA    (SEQ ID NO:6)

TTG CTA GAA AAG-3' anti-sense primer:
5'-CGG GGA TCC TTT CAG GGC CAT TTC    (SEQ ID NO:7)

AG-3'
```

The 352 bp PCR fragment is cloned into the EcoRV site of pBluescript, and excised from pBluescript as a HindIII/BamHI fragment, and sub-cloned into the HindIII/BamHI sites of p74-313, see below, replacing the CaMV 35S promoter.

p74-101: Construct for The Expression of The Synthetic ROS Driven by The Actin2 Promoter (FIG. 2(D)).

The Actin2 promoter (An et al., 1996, *Plant J.*, 10: 107-121) is PCR amplified from genomic DNA of *Arabidopsis thaliana* ecotype Columbia as described in 74-501 (see below) and cloned into pGEM-T-Easy. The 1.2 kbp HindIII/SpeI fragment of the Actin2 promoter is then cloned into p74-313 (see below) as a HindIII/XbaI fragment replacing the CaMV 35S promoter.

Figure 2D:
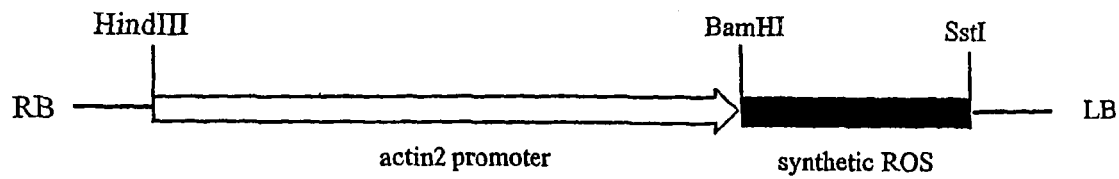
FIG. 2(D) shows the nucleotide construct p74-101 in which an actin2 regulatory region is operatively linked to the protein coding region of synthetic ROS.
Figure 6B:
FIG. 6(B) shows Southern analysis of a plant comprising a second genetic construct, p74-101 (acti-synthetic ROS; see FIG. 2(D) for map).

The various constructs are introduced into *Arabidopsis*, as described above, and transgenic plants are generated. Transformed plants are verified using PCR or Southern analysis. FIG. 6(B) show Southern analysis of transgenic plants comprising a second genetic construct, for example, p74-101 (actin2-synthetic ROS; FIG. 2(D)).

Western Blot Analysis of Repressor Transgenic Lines

The expression of ROS in the repressor lines is assessed by Western blot analysis using a ROS polyclonal antibody. Several lines show high levels of ROS expression. These included plants expressing both the wild type ROS (without any nuclear localization signal) as well as those expressing the synthetic ROS nucleic acid sequences.

Total plant protein extracts are analyzed for the expression of the ROS protein using a polyclonal rabbit anti-ROS antibody. Chemiluminescent detection of antigen-antibody complexes is carried out with goat anti-rabbit IgG secondary antibody conjugated to horseradish poroxidase-conjugated (from Bio-Rad Laboratories) in conjunction with ECL detection reagent (from Ameisham Pharamcia Biotech).

Figure 7:
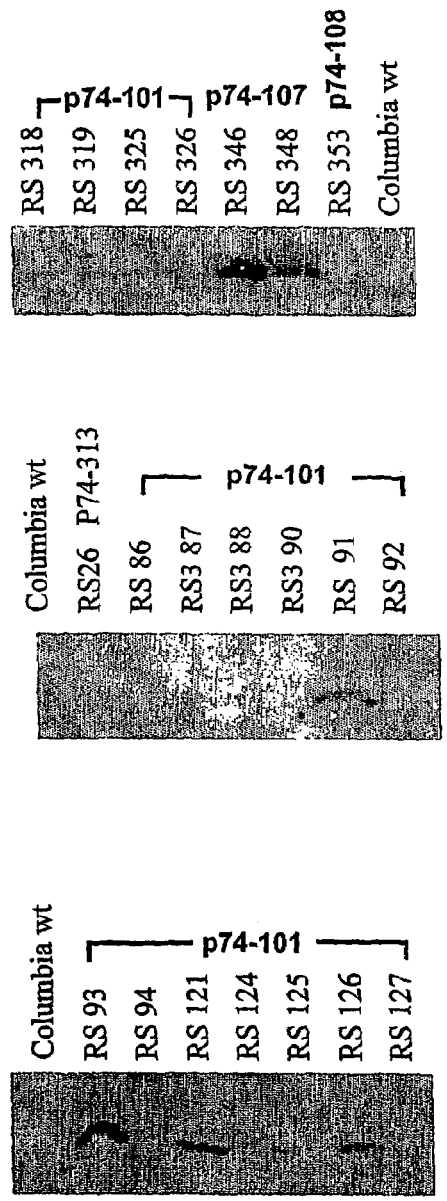
FIG. 7 shows Westerns analysis of ROS expression in transformed *Arabidopsis* plants. Levels of wild type ROS, p7⁴-107 (35S-WTROS; see FIG. 2(A) for map), and synthetic ROS p74-101 (actin2-synROS; see FIG. 2(D) for map) produced in transgenic plants were determined by Western analysis using a ROS polyclonal antibody. *Arabidopsis* var. columbia, was run as a control.

Levels of ROS protein, both wild type ROS (WTROS), for example p74-107 (35S-WTROS; FIG. 2(A)), and synthetic ROS, for example p74-101 (actin2-synROS; FIG. 2(D)), produced in the trangenic plants is determined by Western blot analysis using a ROS polyclonal antibody (FIG. 7).

Representative lines showing various levels of expression were used as a source of pollen for pollination of reporter lines containing single inserts.

Example 3

Constructs Placing a Gene of Interest Under Transcriptional Control of Regulatory Regions that have been Modified to Contain ROS Operator Sites, and Preparation of Reporter Lines p74-315: Construct for The Expression of GUS Gene Driven by a CaMV 35S Promoter Containing a ROS Operator Downstream of TATA Box (FIG. 3(A)).

The BamHI-EcoRV fragment of CAMV 35S promoter in pBI121 is cut out and replaced with a similar synthesized DNA fragment in which the 25 bp immediately downstream of the TATA box were replaced with the ROS operator sequence:

```
    TATATTTCAATTTATTGTAATATA.       (SEQ ID NO:8)
```

Two complementary oligos, ROS-OPDS (SEQ ID NO:9) and ROS-OPDA (SEQ ID NO:10), with built-in BamHI-EcoRV ends, and spanning the BamHI-EcoRV region of CaMV35S, in which the 25 bp immediately downstream of the TATA box are replaced with the ROS operator sequence (SEQ ID NO:8), are annealed together and then ligated into the BamHI-EcoRV sites of CaMV35S.

```
ROS-OPDS:
5'-ATC TCC ACT GAC GTA AGG GAT GAC    (SEQ ID NO:9)

GCA CAA TCC CAC TAT CCT TCG CAA GAC

CCT TCC TCT ATA TAA TAT ATT TCA ATT

TTA TTG TAA TAT AAC ACG GGG GAC TCT

AGA G-3'

ROS-OPDA:
5'-G ATC CTC TAG AGT CCC CCG TGT     (SEQ ID NO:10)

TAT ATT ACA ATA AAA TTG AAA TAT ATT

ATA TAG AGG AAG GGT CTT GCG AAG GAT

AGT GGG ATT GTG CGT CAT CCC TTA CGT

CAG TGG AGA T-3'
```

The p74-315 sequence from the EcoRV site (GAT ATC) to the first codon (ATG) of GUS is shown below (TATA box—lower case in bold; the synthetic ROS sequence—bold caps; a transcription start site—ACA, bold italics; BamHI site—GGA TCC; and the first of GUS, ATG, in italics; are also indicated):

```
5'-GAT ATC TCC ACT GAC GTA AGG GAT    (SEQ ID NO:22)

GAC GCA CAA TCC CAC TAT CCT TCG CAA

GAC CCT TCC TCt ata taA TAT ATT TCA

ATT TTA TTG TAA TAT AACACG GGG GAC

TCT AGA GGA TCC CCG GGT GGT CAG TCC

CTT ATG-3'
``` p74-316: Construct for The Expression of GUS Driven by a CaMV 35S Promoter Containing a ROS Operator Upstream of TATA Box (FIG. 3(B)).

The BamHI-EcoRV fragment of CaMV 35S promoter in pBI121 is cut out and replaced with a similar synthesized DNA fragment in which the 25 bp immediately upstream of the TATA box are replaced with the ROS operator sequence (SEQ ID NO:8). Two complementary oligos, ROS-OPUS (SEQ ID NO:11) and ROS-OPUA (SEQ ID NO:12), with built-in BamHI-EcoRV ends, and spanning the BamHI-EcoRV region of CaMV35S, in which the 25 bp immediately upstream of the TATA box were replaced with a ROS operator sequence (SEQ ID NO:8), are annealed together and then ligated into the BamHI-EcoRV sites of CaMV35S.

```
ROS-OPUS:
5'-ATC TCC ACT GAC GTA AGG GAT GAC    (SEQ ID NO:11)

GCA CAA TCT ATA TTT CAA TTT TAT TGT

AAT ATA CTA TAT AAG GAA GTT CAT TTC

ATT TGG AGA GAA CAC GGG GGA CTC TAG

AG-3'

ROS-OPUA:
5'-G ATC CTC TAG AGT CCC CCG TGT     (SEQ ID NO:12)

TCT CTC CAA ATG AAA TGA ACT TCC TTA

TAT AGT ATA TTA CAA TAA AAT TGA AAT

ATA GAT TGT GCG TCA TCC CTT ACG TCA

GTG GAG AT-3'
```

The p74-316 sequence from the EcoRV site (GAT ATC) to the first codon (ATG) of GUS is shown below (TATA box—lower case in bold; the synthetic ROS sequence—bold caps; a transcription start site—ACA, bold italics; BamHI site—GGA TCC; the first codon of GUS, ATG-italics, are also indicated):

```
5'-GAT ATC TCC ACT GAC GTA AGG GAT    (SEQ ID NO:23)

GAC GCA CAA TCT ATA TTT CAA TTT TAT

TGT AAT ATA Cta tat aAG GAA GTT CAT

TTC ATT TGG AGA GAA CAC GGG GGA CTC

TAG AGG ATC CCC GGG TGG TCA GTC CCT

TAT G-3'
``` p74-309: Construct for The Expression of GUS Driven by a CaMV 35S Promoter Containing ROS Operators Upstream and Downstream of TATA Box (FIG. 3(C)).

The BamHI-EcoRV fragment of CaMV 35S promoter in pBI121 is cut out and replaced with a similar synthesized DNA fragment in which the 25 bp immediately upstream and downstream of the TATA box were replaced with two ROS operator sequences (SEQ ID NO:8). Two complementary oligos, ROS-OPPS (SEQ ID NO: 13) and ROSOPPA (SEQ ID NO:14), with built-in BamHI-EcoRV ends, and spanning the BamHI-EcoRV region of CaMV35S, in which the 25 bp immediately upstream and downstream of the TATA box are replaced with two ROS operator sequences, each comprising the sequence of SEQ ID NO:8 (in italics, below), are annealed together and ligated into the BamHI-EcoRV sites of CaMV35S.

```
ROS-OPPS:
5'-ATC TCC ACT GAC GTA AGG GAT GAC    (SEQ ID NO:13)

GCA CAA TCT ATA TTT CAA TTT TAT TGT

AAT ATA CTA TAT AAT ATA TTT CAA TTT

TAT TGT AAT ATA ACA CGG GGG ACT CTA

GAG-3'

ROS-OPPA:
5'-G ATC CTC TAG AGT CCC CCG TGT      (SEQ ID NO:14)

TAT ATT ACA ATA AAA TTG AAA TAT ATT

ATA TAG TAT ATT ACA ATA AAA TTG AAA

TAT AGA TTG TGC GTC ATC CCT TAC GTC

AGT GGA GAT-3'
```

The p74-309 sequence from the EcoRV site (GAT ATC) to the first codon (ATG) of GUS is shown below (TATA box—lower case in bold; two synthetic ROS sequence—bold caps; a transcription start site—ACA, bold italics; BamHI site—GGA TCC; the first codon of GUS, ATG-italics, are also indicated):

```
5'-GAT ATC TCC ACT GAC GTA AGG GAT   (SEQ ID NO:24)

GAC GCA CAA TCT ATA TTT CAA TTT TAT

TGT AAT ATA Cta tat aAT ATA TTT CAA

TTT TAT TGT AAT ATA ACA CGG GGG ACT

CTA GAG GAT CCC CGG GTG GTC AGT CCC

TTA TG-3'
``` p76-508: Construct for The Expression of The GUS Gene Driven by the tms2 Promoter Containing a ROS Operator (FIG. 4(B)).

The tms2 promoter is PCR amplified from genomic DNA of *Agrobacterium tumefaciens* 33970 using the following primers:

```
sense primer:
5'-TGC GGA TGC ATA AGC TTG CTG ACA   (SEQ ID NO:6)

TTG CTA GAA AAG-3' anti-sense primer:
5'-CGG GGA TCC TTT CAG GGC CAT TTC   (SEQ ID NO:7)

AG-3'
```

The 352 bp PCR fragment is cloned into the EcoRV site of pBluescript, and sub-cloned into pGEM-7Zf(+). Two complementary oligos, ROS-OP1 (SEQ ID NO:15) and ROS-OP2 (SEQ ID NO:16), containing two ROS operators (in italics, below), are annealed together and cloned into pGEM-7Zf(+) as a BamHI/ClaI fragment at the 3' end of the tms2 promoter. This promoter/operator fragment is then sub-cloned into pBI121 as a HindIII/XbaI fragment, replacing the CaMV 35S promoter fragment.

```
ROS-OP1:
5'-GAT CCT ATA TTT CAA TTT TAT TGT    (SEQ ID NO:15)

AAT ATA GCT ATA TTT CAA TTT TAT TGT

AAT ATA AT-3'

ROS-OP2:
5'-CGA TTA TAT TAC AAT AAA ATT GAA    (SEQ ID NO:16)

ATA TAG CTA TAT TAC AAT AAA ATT GAA

ATA TAG-3'.
```

As a control, p76-507 comprising a tms2 promoter (without any operator sequence) fused to GUS (FIG. 4(A)), is also prepared.

p74-501: Construct for The Expression of The GUS Gene Driven by The Actin2 Promoter Containing a ROS operator (FIG. 5(B)).

The Actin2 promoter is PCR amplified from genomic DNA of *Arabidopsis thaliana* ecotype Columbia using the following primers:

```
Sense primer:
                                      (SEQ ID NO:17)
   5'-AAG CTT ATG TAT GCA AGA GTC AGC-3'
            SpeI Anti-sense primer:
                                      (SEQ ID NO:18)
   5'-TTG ACT AGT ATC AGC CTC AGC CAT-3'
```

Figure 5C:
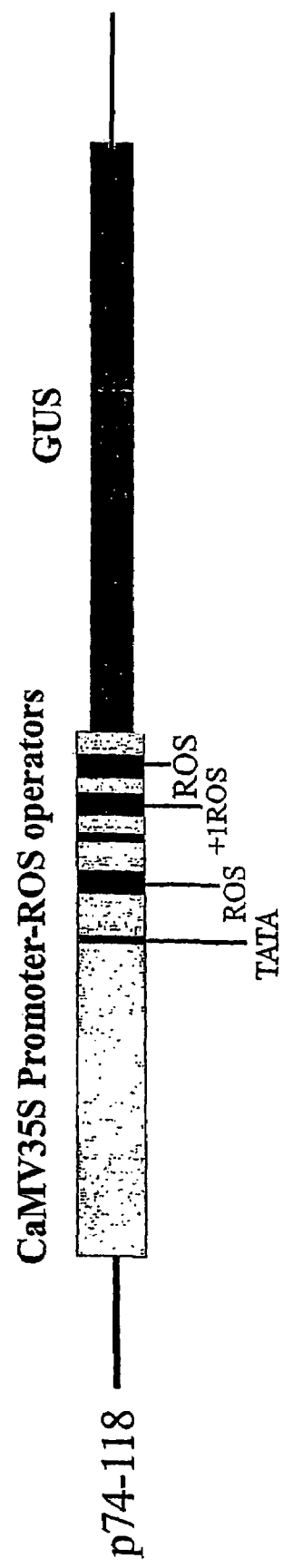
FIG. 5C shows construct p74-118 comprising a 35S regulatory region with three ROS operator sites downstream from the TATA box. The 35S regulatory region is operatively linked to the gene of interest (GUS).

The PCR fragment is cloned into pGEM-T-Easy. Two complementary oligos, ROS-OP1 (SEQ ID NO:15) and ROS-OP2 (SEQ ID NO:16), with built-in BamHI and ClaI sites, and containing two ROS operators, are annealed together and inserted into the Actin2 promoter at the BglII/Cla I sites replacing the BglII/ClaI fragment. This modified promoter is inserted into pBI121vector as a HindIII/BamHI fragment.

p74-118 Construct for The Expression of GUS Driven by a CaMV 35S Promoter Containing three ROS Operators Downstream of TATA Box (FIG. 5(C)).

The BamHI-EcoRV fragment of CaMV 35S promoter in pBI121 is cut out and replaced with a similar synthesized DNA fragment in which a region downstream of the TATA box was replaced with three ROS operator sequences (SEQ ID NO:25). The first of the three synthetic ROS operator sequences is positioned immediatley of the TAT box, the other two ROS operator sequence are located downstream of the trasncriptional start site (ACA). Two complementary oligos with built-in BamHI-EcoRV ends were prepared as describe above for the other constructs were annealed together and ligated into the BamHI-EcoRV sites of CaMV35S.

The p74-118 sequence from the EcoRV site (GATATC) to the first codon (ATG) of GUS is shown below (TATA box—lower case in bold; three synthetic ROS sequence—bold caps; a transcription start site—ACA, bold italics; BamHI site—GGATCC; the first codon of GUS, ATG-italics, are also indicated):

```
5'-GAT ATC TCC ACT GAC GTA AGG GAT      (SEQ ID NO:25)

GAC GCA CAA TCC CAC TAT CCT TCG CAA

GAC CCT TCC TCt ata taA TAT ATT TCA

ATT TTA TTG TAA TAT AAC ACG GGG GAC

TCT AGA GGA TCC TAT ATT TCA ATT TTA

TTG TAA TAT AGC TAT ATT TCA ATT TTA

TTG TAA TAT AAT CGA TTT CGA ACC CGG

GGT ACC GAA TTC CTC GAG TCT AGA GGA

TCC CCG GGT GGT CAG TCC CTT ATG-3'
```

As a control, p75-101, comprising an actin2 promoter (without any operator sequence) fused to GUS (FIG. 5(A)), is also prepared.

The various constructs are introduced into *Arabidopsis*, as described above, and transgenic plants are generated. Transformed plants are verified using PCR or Southern analysis. FIG. 6(A) show Southern analysis of transgenic plants comprising a first genetic construct, for example, p74-309 (35S-operator sequence-GUS, FIG. 3(C)).

GUS Expression Assays on Reporter Transgenic Lines

In order to assess the activity of the modified regulatory regions, the level of expression of the GUS gene is assayed. Leaf tissues (approximately 10 mg) from putative positive transformants are placed into a microtitre plate containing 100 ul of GUS staining buffer (100 mM KPO$_4$, 1 mM EDTA, 0.5 mM K-ferricyanide, 0.5 mM K-ferrocyanide, 0.1% Triton X-100, 1 mM 5-bromo-4-chloro-3-indolyl glucuronide), and vacuum-infiltrated for one hour. The plate is covered and incubated at 37° C. overnight. Tissues are destained when necessary using 95% ethanol and color reaction is evaluated either visually or with a microscope.

For the modified 35S promoter, 45 lines had high GUS expression levels. These include 15 lines containing the ROS operator upstream of the TATA box, 24 lines containing the ROS operator downstream of the TATA box and six lines containing the ROS operator upstream and downstream of the TATA box. Using the actin2 promoter, 8 lines containing the ROS operator displayed high levels of GUS activity. An example of GUS expression in a plant transformed with p74-501 (actin-ROS operator sequence:GUS), is shown in FIG. 8.

Single copy transformants expressing various levels of GUS activity are used for crossing with repressor lines prepared in Example 2, as outlined in Example 4.

Example 4

Crossing of Transgenic Lines Containing ROS Repressor Constructs with Transgenic Lines Containing GUS Reporter Constructs Transgenic *Arabidopsis* lines containing repressor constructs (second genetic constructs) are crossed with lines containing appropriate reporter (GUS) constructs (first genetic constructs). To perform the crossing, open flowers are removed from plants of the reporter lines. Fully formed buds of plants of the repressor lines are gently opened and emasculated by removing all stamens. The stigmas are then pollinated with pollen from plants of the repressor lines and pollinated buds are tagged and bagged. Once siliques formed, the bags are removed, and mature seeds are collected. Plants generated from these seeds are then used to determine the level of reporter gene (GUS) repression by GUS staining. Levels of GUS expression in the hybrid lines are compared to those of the original reporter lines. Plants showing a decrease in GUS expression levels are further characterized using PCR, Southern and Northern analysis.

Figure 9:
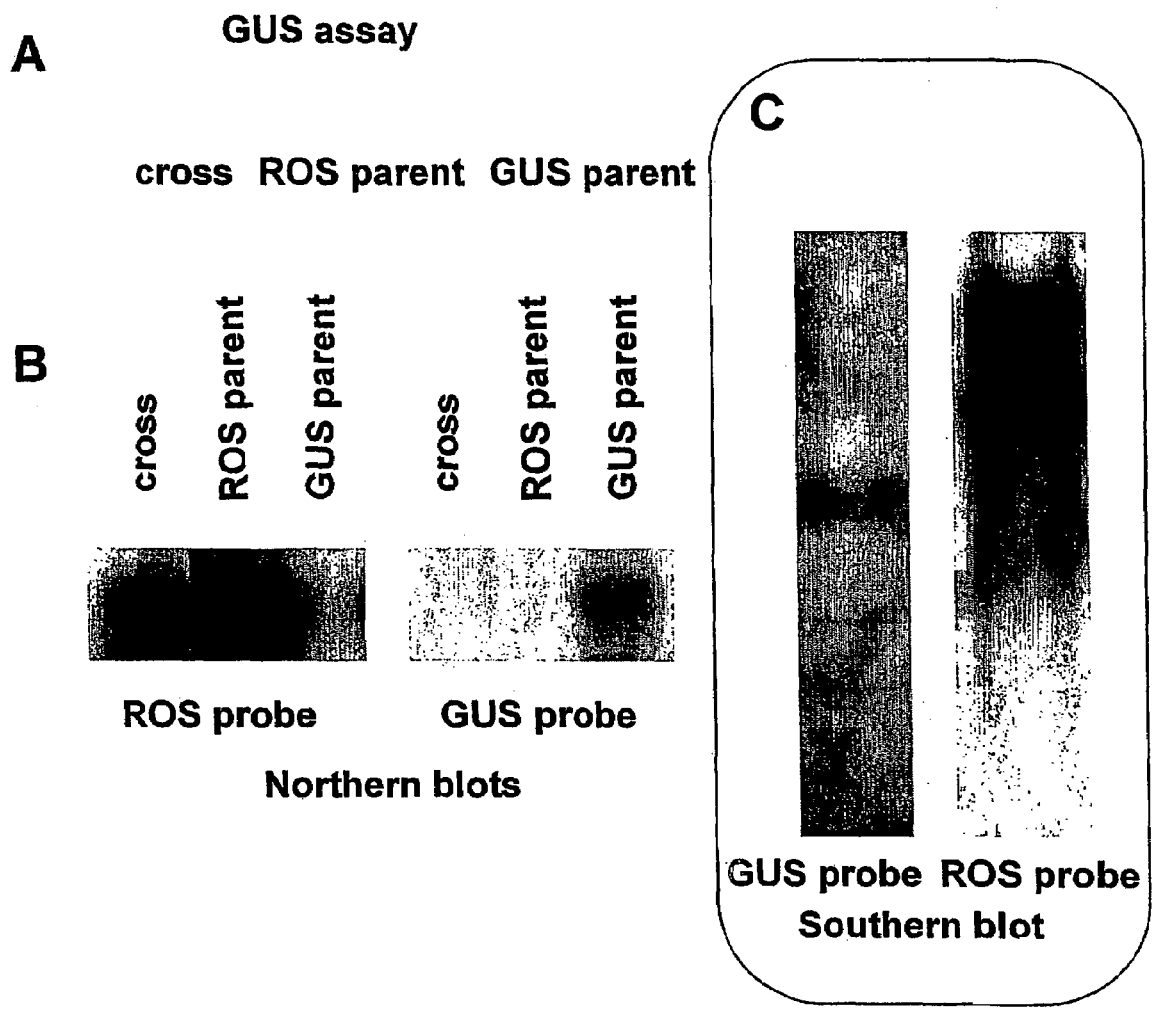
FIG. 9 shows regulation of a gene of interest in progeny plants arising from a cross between a ROS parent plant (expressing p74-101, FIG. 2D; and example of a second nucleotide sequence) and a plant expressing a gene of interest under the control of a regulatory region comprising ROS operator sequences (GUS parent expressing p74-118, FIG. 5C; and example of a first nucleotide sequence).

Results of a cross between a transgenic line expressing synthetic ROS (p74-101-FIG. 2D) and GUS (p74-118 (FIG. 5C) are presented in FIG. 9.

GUS activity (FIG. 9A) is only observed in plants expressing GUS (termed GUS parent in FIG. 9, expressing p74-118). The plant expressing ROS (ROS parent, expressing p74-101) exhibited no GUS expression. This result is as expected, since this plant is not transformed with the GUS construct. Of interest, however, is that the plant produced as a result of a cross between the GUS and ROS parents did not exhibit GUS activity.

Northern analysis (FIG. 9B) demonstrates that GUS expression is consistent with the GUS assay (FIG. 9A), in that oily the GUS parent expressed GUS RNA, while no GUS expression was observed in the ROS parent or the progeny arising from a cross between the ROS and GUS parents. Similarly, as expected, no ROS expression was detected in the GUS parent. ROS expression was observed in the ROS parent and in the cross between the ROS and GUS parents.

Southern analysis of the progeny of the cross between the GUS and ROS parents demonstrates that the cross comprised genes encoding both. GUS and ROS (FIG. 9C).

These data demonstrate ROS repression of a gene of interest. The progeny of the cross between the ROS and GUS parent lines, comprising both the GUS and ROS gene, expresses the ROS repressor, which binds the operator sequence thereby inhibiting the expression of the gene of interest, in this case GUS. Inhibition of GUS expression was observed at the RNA and protein levels, and no enzyme activity was present in the progeny plants.

FIGS. 1A-D, shows results of the crosses described in Table 5, between a range of repressor and reporter plants (plants expressing Tag protein). Maps of the constructs listed in Table 5 are shown in FIGS. 10A and B.

TABLE 5

Crossing of lines expressing reporter lines expressing a protein of interest with plant lines expressing the repressor protein

| Crosses | Constructs<br>Female X male | Parental lines<br>Female X male parent |
|---|---|---|
| Cross1(C1) | 74-316 X 74-101 | P1GUS X P1ROS |
| Cross2(C2) | 74-101 X 74-117 | P2ROS X P2GUS |
| Cross3(C3) | 74-118 X 74-101 | P3GUS X P3ROS |
| Cross4(C4) | 74-117 X 74-101 | P2GUS X P2ROS |

Northern blot analysis of total RNA (~4.5 g) isolated from *Arabidopsis* parental lines including reporter plants expressing a protein of interest, in this example GUS, and crosses between the parental lines as indicated in Table 5 was performed. Results of these analysis is shown in FIGS. 11A-D. The results of GUS expression using GUS as a probe for crosses C1-C5 are shown in FIG. 11A. Results of ROS expression, using ROS as a probe for crosses C1-C5 are shown in FIG. 11B. FIG. 11C shows the loading of the RNA gel, and FIG. 11D shows quantification of the densities of the bands generated in the Northern analysis of FIG. 11A using a GUS probe.

The parental lines expressing ROS, and all of the crosses that were made to ROS exhibited ROS expression as indicated in FIG. 11B. No ROS expression is observed in parental lines expressing GUS since these lines do not comprise a ROS construct. With reference to FIG. 11A, GUS maximal expression is observed in parental lines expressing the reporter construct (GUS P1-P3 and P5); however, a range of reduced GUS activity is observed in plants that were crossed (lanes marked C1-C5) with a plants expressing a repressor construct. The range of reduced GUS activity varied with reduction of the maximal. GUS activity observed in lines C2D and C2G.

In FIG. 11D, lanes P1 GUS, P2 GUS, P3 GUS, P4 GUS, P5 GUS, exhibit GUS expression of the parent expressing the first nucleotide sequence (i.e. p74-316, p74-117, p74-118, p74-117 and p74-501, respectively). These plants exhibit maximum expression of GUS RNA. Lanes P1 ROS, P2 ROS, P3 ROS, P4 ROS (comprising p74-101 or p74-313) exhibit background levels of GUS RNA, as these plants do not comprise any sequence resulting in GUS expression. Progeny of all crosses between plants expressing the first nucleotide sequence (p74-316, p74-117, p74-118, p74-117 and p74-501) and plants expressing the second nucleotide sequence (p74-101 or p74-313) resulted in reduced expression of GUS (the first coding region, 30) of from about 30% (e.g. for C1A) to about 90% (for C2G).

These results show that expression of a protein of interest can be controlled using the repressor mediated system as described herein.

FIG. 13 represents a northern analysis of plants obtained from crossing transgenic *Brassica* lines containing repressor constructs (second genetic constructs) with lines containing appropriate reporter (GUS) constructs (first genetic constructs). *Agrobacterium*-mediated transformation of *B. napus* was carried out as described in Moloney et al., Plant Cell Rep. 8:238-242 (1989) with modifications. Seeds were sterilized and then plated on ½ strength hormone-free MS medium (Sigma) with 1% sucrose in 15×60 mm petri dishes. Seeds were then transferred, with the lid removed, into Magenta GA-7 vessels (temperature of 25 degrees C., with 16 h light/8 h dark and a light intensity of 70-80 microE.

Cotyledons were excised from 4-day old seedlings and soaked in BASE solution (4.3 g/L MS (GIBCO BRL), 10 ml 100× B5 Vitamins (0.1 g/L nicotinic acid, 1.0 g/L thiamine-HCl, 0.1 g/L pyridoxine-HCl, 10 g/L m-inositol), 2% sucrose, 1 mg/L 2,4-D, pH 5.8; 1% DMSO and 200 microM acetosyringone added after autoclaving) containing *Agrobacterium* cells comprising a recombinant plant transformation vector. Most of the BASE solution was removed and the cotyledons were incubated at 28 degrees C. for 2 days in the dark. The dishes containing the cotyledons were then transferred to 4 degrees C. for 3-4 days in the dark. Cotyledons were transferred to plates containing MS B5 selection medium (4.3 g/L MS, 10 ml 100× B5 Vitamins, 3% sucrose, 4 mg/L benzyl adenine (BA) ph 5.8; timentin (300 Fg/ml) and kanamycin (20 Fg/ml) were added after autoclaving) and left at 25 degrees C., 16 h light/8 dark with lighting to 70-100 microE. Shoots were transferred to Magenta GA-7 vessels containing MS B5 selection medium without BA. When shoots were sufficiently big they were transferred to Magenta GA-7 vessels containing rooting medium and upon development of a good root system plantlets were removed from the vessels and transferred to moist potting soil.

The genetic constructs that were used to transform parental cell lines were p74-114 and p74-101. As shown in FIG. 12B p74-114 is a construct comprising a region encoding GUS operatively linked to a CaMV 35S regulatory region containing one ROS operator sequence upstream and three ROS operator sequences downstream of TATA Box.

p74-114: Construct for The Expression of GUS Driven by a CaMV 35S Promoter Containing One ROS Operator Upstream and Three ROS Operators Downstream of TATA Box:

In order to construct p74-114 (see FIG. 12B) the BamHI-EcoRV fragment of CaMV 35S promoter in pBI121 is cut out and replaced with a similar synthesized DNA fragment in which a region upstream and downstream of the TATA box was replaced with four ROS operator sequences (SEQ ID NO:8). The first of the four synthetic ROS operator sequences is positioned 25 bp immediately upstream of the TATA box. The second of the four synthetic ROS operator sequences is positioned 25 bp immediately downstream of the TATA box. The other two ROS operator sequences are located downstream of the transcriptional start site (ACA). Two complementary oligos (SEQ ID NO:13 and 14) with built-in BamHI-EcoRV ends were prepared as described above for the other constructs, were annealed together and ligated into the BamHI-EcoRV sites of CaMV 35S. The p74-114 sequence from the EcoRV site (GAT ATC) to the first codon (ATG) of GUS is shown below (SEQ ID NO:45); TATA box—lower case in bold: the synthetic ROS sequence—bold caps; a transcription start site—ACA, bold italics: BamHI site—GGA TCC; the first codon of GUS, ATG—italics, are also indicated);

```
5' GAT ATC TCC ACT GAC GTA AGG GAT     (SEQ ID NO:45)

GAC GCA CAA TCT ATA TTT CAA TTT TAT

TGT AAT ATA Cta tat aAT ATA TTT CAA

TTT TAT TGT AAT ATA ACA CGG GGG ACT

CTA GAG GAT CCT ATA TTT CAA TTT TAT

TGT AAT ATA GCT ATA TTT CAA TTT TAT

TGT AAT ATA ATC GAT TTC GAA CCC GGG

GTA CCG AAT TCC TCG AGT CTA GAG GAT

CCC CGG GTG GTC AGT CCC TTA TG-3'
```

The engineering of the p74-101 (FIG. 12A) construct for synROS expression under actin2 promoter has been described above in Example 2.

Parental *Brassica napus* lines separately comprising p74-101 or p74-114 are crossed to produce hybrid lines comprising both p74-101 and p4-114. Crosses performed are as follows: C1 and C2 are p74-114x p74-101. P1GUS is the GUS parent plant for C1. P2GUS is GUS parent plant for C2. PROS is ROS parent plant for crosses C1 and C2. Levels of GUS expression in the hybrid lines are compared to those of the original parent lines by northern analysis as shown in FIG. 13. FIG. 13 demonstrates that high GUS expression, greater than 100, only occurs in the GUS parental line P1GUS, while no GUS expression was observed in the ROS parent PROS, and GUS expression is reduced in progeny arising from a cross between the ROS and GUS parents, C1 and C2. Similarly, as expected, no ROS expression was detected in the GUS parental lines, P1GUS and P2GUS. ROS expression was observed in the ROS parent and in the cross between the ROS and GUS parents.

These data further demonstrate ROS repression of a gene of interest in Brassicacae. The progeny of the cross between the ROS and GUS parent lines, comprising both the GUS and ROS gene, expresses the ROS repressor, which binds the operator sequence thereby inhibiting the expression of the gene of interest, in this case GUS.

These data demonstrate that expression of a gene of interest can be controlled using the repressor mediated system as described herein.

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A nucleic acid molecule encoding a ROS repressor optimized for plant codon usage and exhibiting ROS operator binding activity, ROS repressor activity, or both ROS operator binding activity and ROS repressor activity, wherein said nucleic acid molecule comprises the nucleotide sequence of SEQ ID NO:2 or SEQ ID NO: 3.

2. A genetic construct comprising a regulatory region in operative association with the nucleic acid molecule of claim 1.

3. The nucleic acid molecule of claim 1, further comprising a nucleic acid sequence encoding a nuclear localization signal fused to said nucleic acid molecule.

4. The genetic construct of claim 2, further comprising a nucleic acid sequence encoding a nuclear localization signal fused to said nucleic acid molecule.

5. A plant comprising the genetic construct of claim 2.

6. A plant comprising the genetic construct of claim 4.

7. A seed comprising the genetic construct of claim 2.

8. A seed comprising the genetic construct of claim 4.

9. A plant comprising;
  i) a first genetic construct comprising a genetic construct comprising a regulatory region operatively linked to a gene of interest and one, or more than one, ROS operator sequence capable of controlling the activity of said regulatory region, wherein said regulatory region is functional in plants, and
  ii) a second genetic construct comprising a regulatory region in operative association with the nucleic acid molecule of claim 1.

10. The plant as defined in claim 9, wherein said second genetic construct further comprises a nuclear localization signal fused to said nucleic acid molecule [or derivative thereof].

11. The plant of claim 9, wherein said gene of interest encodes a protein selected from the group consisting of one or more enzymes involved in fiber biosynthesis, one or more enzymes involved in glucosinolate biosynthesis, one or more enzymes involved in phytotoxin biosynthesis, caffeic o-methyltransferase, indole acetamide hydrolase, and phosphinothricin acetyl transferase.

12. A vector comprising;
  i) a first genetic construct comprising a first nucleic acid molecule comprising a first regulatory region operatively linked to a gene of interest and one, or more than one, ROS operator sequence capable of controlling the activity of said first regulatory region, wherein said first regulatory region is functional in plants; and
  ii) a second genetic construct comprising a second regulatory region in operative association with the nucleic acid molecule of claim 1.

13. The vector as defined in claim 12, wherein said second genetic construct further comprises a nuclear localization signal fused to said nucleic acid molecule [or derivative thereof].

14. The vector of claim 12, wherein said first and second regulatory regions are either the same or different and are selected from the group consisting of a constitutive promoter, an inducible promoter, a tissue specific promoter, and a developmental promoter.

15. A plant comprising the vector of claim 13.

16. A plant comprising the vector of claim 14.

17. The plant of claim 9, wherein said at least one ROS operator sequence comprises the nucleotide sequence of SEQ ID NO:20.

18. The plant as defined in claim 5, wherein said plant is selected from the group consisting of canola, *Brassica* spp., maize, tobacco, alfalfa, potato, ginseng, pea, oat, rice, soybean, wheat, barley, sunflower, and cotton.

19. The plant as defined in claim 6, wherein said plant is selected from the group consisting of canola, *Brassica* spp., maize, tobacco, alfalfa, potato, ginseng, pea, oat, rice, soybean, wheat, barley, sunflower, and cotton.

20. The plant as defined in claim 9, wherein said plant is selected from the group consisting of canola, *Brassica* spp., maize, tobacco, alfalfa, potato, ginseng, pea, oat, rice, soybean, wheat, barley, sunflower, and cotton.

* * * * *

UNITED STATES PATENT AND TRADEMARK OFFICE
CERTIFICATE OF CORRECTION

PATENT NO. : 7,521,595 B2
APPLICATION NO. : 10/995951
DATED : April 21, 2009
INVENTOR(S) : Hannoufa et al.

It is certified that error appears in the above-identified patent and that said Letters Patent is hereby corrected as shown below:

In the claims:

Claim 10, Col. 54, Lines 36 & 37: Delete "acid molecule [or derivative thereof]" and insert -- acid molecule. --

Claim 13, Col. 54, Lines 58 & 59: Delete "acid molecule [or derivative thereof]" and insert -- acid molecule. --

Signed and Sealed this

Twenty-first Day of July, 2009

JOHN DOLL
*Acting Director of the United States Patent and Trademark Office*